(12) United States Patent
Ivanov

(10) Patent No.: US 6,569,681 B1
(45) Date of Patent: May 27, 2003

(54) METHODS OF IMPROVING HOMOLOGOUS RECOMBINATION

(75) Inventor: Evguenii Ivanov, Sharon, MA (US)

(73) Assignee: Transkaryotic Therapies, Inc., Cambridge, MA (US)

( * ) Notice: Subject to any disclaimer, the term of this patent is extended or adjusted under 35 U.S.C. 154(b) by 0 days.

(21) Appl. No.: 09/525,160

(22) Filed: Mar. 14, 2000

(51) Int. Cl.[7] ........................... C12N 15/87; C12N 15/63
(52) U.S. Cl. ........................ 435/463; 435/455; 435/462
(58) Field of Search .............................. 435/463, 462, 435/455; 424/93.2

(56) References Cited

U.S. PATENT DOCUMENTS

| | | | |
|---|---|---|---|
| 5,272,071 A | 12/1993 | Chappel | .................. 435/172.3 |
| 5,641,670 A | 6/1997 | Treco et al. | |
| 5,780,296 A | 7/1998 | Holloman et al. | |
| 5,945,339 A | 8/1999 | Holloman et al. | |
| 6,010,908 A | 1/2000 | Gruenert et al. | |
| 6,251,674 B1 * | 6/2001 | Tobin et al. | ................. 435/400 |
| 6,255,113 B1 * | 7/2001 | Zarling et al. | ............... 435/463 |

FOREIGN PATENT DOCUMENTS

| | | |
|---|---|---|
| WO | WO 98/30902 | 7/1998 |
| WO | WO 98/30903 | 7/1998 |
| WO | WO 99/25829 | 5/1999 |
| WO | WO 99/30902 | 5/1999 |
| WO | WO 99/33971 | 7/1999 |
| WO | WO 00/12716 | 3/2000 |
| WO | WO 00/68404 | 11/2000 |

OTHER PUBLICATIONS

Verma et al., Gene therapy–promises, problems and prospects, 1997, NATURE, vol. 389, pp. 239–242.*

Orkin et al., Report and recommendations of the panel to assess the NIH investment in research on gene therapy, 1995, NIH.*

Critchlow et al. 1997 "Mammalian DNA Double–Strand Break Repair Protein XRCC4 Interacts with DNA Ligase IV" Current Biology, Current Science, vol. 7 588–598.

Kabotyanski et al. 1998 "Double–strand break repair in Ku86– and XRCC4–deficient cells" Nucleic Acids Research vol. 26 No. 23, 5333–5342.

Milne et al. "Mutations in two Ku homologs define a DNA end–joining repair pathway in Saccharomyces cerevisiae" Molecular and Cellular Biology vol. 16 No. 8, 4189–4198 XP002178015.

Petrini et al. 1999 "The Mammalian Mre11–Rad50–Nbs1 Protein Complex: Intergration of Functions in the Cellular DNA–Damage Response" American Journal of Human Genetics, University of Chicago Press, Chicago, US vol. 64, 1264–1269, xp002150324.

Teo Soo–Hwang et al. 2000 "Lif1p targets the DNA liagase Lig4p to sites of DNA double–strand breaks" Current Biology vol. 10 No. 3 165–168 XP002178014.

Tomkinson et al. 1998 "Structure and Function of Mammalian DNA Ligases" Mutation Research, Amsterdam vol. 407 1–9 XP002065035.

Tsukamoto Y et al. 1996 "Hdfl, a yeast Ku–protein homologue, is involved in illegitimate recombination, but not in homologous recombination" Nucleic Acids Research, Oxford University vol. 24, No. 11 2067–2072.

Baumann et al. 1998 "DNA end–joining catalyzed by human cell–free extracts" *Proceedings of the National Academy of Sciences* 95(24): 14066–14070.

Bendixen et al. 1994 "Identification of a Mouse Homologue of the *Saccharomyces cerevisiae* Recombination and Repair Gene, RAD52" *Genomics* 23(1):300–303.

Bertolotti, R.1996 "Recombinase–mediated gene therapy; strategies based on lesch–Nyhan mutants for gene repair/inactivation using human RAD51 nucleoprotein filaments" *Biogenic Amines* 12(6): 487–498.

Benson et al. 1998 "Synergistic actions of Rad51 and Rad52 in recombination an DNA repair" *NATURE* 391: 401–403.

Cole–Strauss et al. 1996 "correction of the Mutation Responsible for Sickle Cell Anemia by an RNA–DNA Oligonucleotide" 273: 1386–1389.

De Wind et al. 1995 "Inactivation of the Mouse Msh2 Gene Results in Mismatch Repair Deficiency, Methylation Tolerance, Hyperrecombintion, and Predisposition to Cancer" *Cell* 82(2): 321–330.

Haber et al. 1998 "The Many Interfaces of Mre11" *Cell* 95(5): 583–586.

K. Kunzelman et al. 1996 "Gene targeting of CFTR DNA in CF epithelial cells" *Cell Therapy* 3: 859–867.

Kren et al. 1999 "Correction of the UDP–glucuronosyltransferase gene defect in the Gunn rat model of Crigler–Najjar syndrome type I with a chimeric oligonucleotide" *Proc. Natl. Acad. Sci.–Medical Sciences* 96: 10349–10354.

D.F.R. Muris et al. 1994 "Cloning of human and mouse genes homologous to RAD52, a yeast gene involved in DNA repair and recombination" *Mutation Research, DNA Repair* 315: 295–305.

(List continued on next page.)

*Primary Examiner*—Deborah J. Reynolds
*Assistant Examiner*—Valarie Bertoglio
(74) *Attorney, Agent, or Firm*—Fish & Richardson PC

(57) ABSTRACT

The invention features a method of promoting an alteration at a selected site in a target DNA, e.g., in the chromosomal DNA of a cell. The method includes providing, at the site: (a) a double stranded DNA sequence which includes a selected DNA sequence; (b) an agent which enhances homologous recombination, e.g., a Rad52 protein or a functional fragment thereof; and (c) an agent which inhibits non-homologous end joining, e.g., an agent which inactivates Ku such as an anti-Ku antibody or a Ku-binding oligomer or polymer, and allowing the alteration to occur. The agent which inhibits non-homologous end joining, e.g., a Ku inactivating agent such as an anti-Ku antibody, is preferably provided locally. Components (a), (b), and (c) can be introduced together, which is preferred, or separately.

46 Claims, No Drawings

OTHER PUBLICATIONS

Park 1995 "Expression of human RAD52 Confers Resistance to Ionizing Radiation in Mammalian Cells" *The Journal of Biological Chemistry* 270(26): 15467–15470.

RJ Yanez et al. 1999 "Gene targeting is enhanced in human cells overexpressing hRAD51" *Gene Therapy* 6: 1282–1290.

RJ Yanez et al. 1998 "Therapeutic gene targeting" *Gene Therapy* 5: 149–159.

Shore 1998 "Telomeres—Unsticky Ends" *SCIENCE* 281(5384): 1818–1819.

Shen et al. 1995 "The Human and Mouse Homologs of the Yeast RAD52 Gene:cDNA Cloning, Sequence Analysis, Assignment to Human Chromosome 12p12.2–p13, and mRNA Expression in Mouse Tissues" *GENOMICS* 25(1): 199–206.

Tuddenham et al. 1994 "Hemophilia A: database of nucleotide substitutions, deletions, insertions and rearrangements of the factor VIII gene, second edition" 22(22): 4851–4868.

Takiguchi et al. 1996 "Genomic Structure and Chromosomal Assignment of the Mouse Ku70 Gene" *GENOMICS* 35(1): 129–135.

Van Dyck et al. 1998 "Visualisation of Human Rad52 Protein and its Complexes with hRad51 and DNA" *JMB* 284(4): 851–1242.

Van Dyck et al. 1999 "Binding of double–strand breaks in DNA by human Rad52 protein" *NATURE* 398:728–731.

Zhang et al. 1997 "A new approach to gene therapy" *Blood coagulation and Fibrinolysis* 8(2): S39–S42.

* cited by examiner

SEQUENCE LISTING

```
<160> NUMBER OF SEQ ID NOS: 10

<210> SEQ ID NO 1
<211> LENGTH: 7622
<212> TYPE: DNA
<213> ORGANISM: Homo sapiens

<400> SEQUENCE: 1
ggatccgaga acatagaagg agcaggtaat ttatcaaggc atgaacacgg gtgcttaatt        60
tcctattttg aggccaggca tggtggctca cacctgtaat cccaacactt taggaagcca       120
aggtgggtgg attgcttgag tctaggattt tgagaccagc ctggccaaca tggcgaaatc       180
ctgtctctac taaaaatact aaaattaacc agtcatggtg gtggtgtgcc tttagtccca       240
gctactctgg tggctgaggc acaagaatca cttgaacctg ggaggcagag gttgcagtga       300
gctgagactg tgccacttca ctccagcctg ggtgacagag taagattctg tctcaaaaaa       360
tatgtatata tacacacata taatagatac ataaacatat atacatatat aatatatata       420
tatatatatt atatataata tataaacata tataaatata tatatatata tatatatata       480
tatataaacc aaacataaag gaataatttt gggggaaaat cttcataaat gaaagaacaa       540
cataggctgt tgagtatatg cacagaaatt caagagatct tccagcaatt gaagacattg       600
gtttaccaga attcacaaaa gaagtcagct gtgcatttaa agtagaatgt gatgagtgtt       660
accactgagg taggaactgg gaactaagga agcgtaagac agaaagtgct gaactgagag       720
ttgggcattg gaggctgtgt aaggcagggt aagtgaatgt ctcctagaag ctaccttaa       780 atggagtttt gaagtacttg taggagtagc ttaggtgaaa agaagaggag aaacatgtat       840
caggcagagg gactagaacc ttattacctt caaagaagaa gcaaaaagaa tacatgtgac       900
tttgaggtgg tgggaggtgc tttaagccaa tataggtgaa tttgacatag gacttccta       960 aataatgttc ggtcatttgt taaatattga gtgatatatc actgtattaa agcccaagag      1020
ttgcttttat atagaaagaa gaaaaaagcc caagagagtt ttatttctag agggaatatt      1080
ttctagaaat aaaggaaggt gtatcagcca gtttctagtc aggaaaacag aaatcacacc      1140
tgatatgcaa aatagaggaa aatcaggaa ttcattaatc cagagatttg gttgctcaag      1200
tattagattg ctgaaaagcc agacagggaa tatgaggcaa tcagagataa gtattagtga      1260
caagctccat ttatgtgcag gattggaggg acataggtgg ggttcccaga agccagaagg      1320
tgagaccacc tagcagaagc tcaaaccaca gctggggttt cctcacaaaa gctgggacca      1380
ccaggaggag ctgtccaatg ggatctggag ccaggagat catgcagtca ctaccaggaa      1440
```

-continued

```
gggaagcaga atgtaaaagg tagagagaaa tactccaact gcttccttgc attcactttc    1500
caatctccat tcacaaaggc aaaaacctgc taatacagca gagtgggaaa agcagcctgc    1560
caaggtcctt tctcccacaa aacagagcac aaaaccaagc aaaaacaagg aatgcatttg    1620
atagcaaaca ggctatggac caacccaaca taaaagaaat gatgagtgat ttcttttttc    1680
atttggttca agaaaagtat ttcagtaact attatgtaac agaaattcta tttattttgg    1740
ggaattcaaa ggtgaataaa aaagaactct aaattttat caataaaata tttcaaaaac    1800
ctcaatgaga gtaatggcat taactagcaa atatgctaat gagatgagct agccataaga    1860
ggcttagaat tgagagaaag gtctgggggc ctcttgacag gccaaattca gagctgtttg    1920
tgggaatctc tgacctaact gcaggtgaaa atataaatat gggcatttag aatagtggcc    1980
caaactttgg atgatttctg tcttgggtc tctccaatta atgggattga tgagaactgt    2040
agaccactga ggtcaccatg gctcaatgaa tagtcccctg gctttggagt caaactgacc    2100
tgaatatgaa ccccagcttt gctacttaca ggttgcattt atcctcagtt ttctcatctt    2160
tcaaagaaga acagtaactt cttaaaaagg ttattgtagg ctgggtgcag tggctcacgc    2220
ctgtaatcgc agcactttgg gaggcggagg ctagtggatc acttgaggcc aggagttgga    2280
aactagcctg gccaacatgg tgaaactctg tctctacaaa aagaaattta aaaattttg    2340 ctgggtgtgg tggcacacac ctggaattcc agctacctgg gaggccgagg catgagcatc    2400
acttgagtct ggaaagcaga gggttgcagt gagccaagat tgtaccactg tactcaagcc    2460
tgggtgacac agtgagacct tgtctaaaaa aaaaaaaggt tattgtgtta ttgtaaatat    2520
tgtatatgaa cttctatta acatgtttag ttaaatgcct gtgtaattgt ccaatgtgct    2580
cttctagctc actgcacaga caaaactgat tcactgaaat catggaattg cagcaaagaa    2640
caaatctaat taatgtaggt caaacgggag gactggagtt attattcaaa tcagtctccc    2700
tgaaaactca gaggctaggg ttttatggat aatttggtgg gcaggggact agggaatggg    2760
tgctgctgat tggttgggga atgaaatagt aagattgtgg aaaactgtcc tccttcattg    2820
agtctgcttc cgggtgtagg ccacacgacc agttgagtca tgaagcatgc gtccaagtgg    2880
agtcagtttg ttgccagaat gcaaaagcct gaaaaatgtc tcaaatgatc aactgtaggc    2940
tccacaataa tgatattatc tataggagca attggggaag taacaaatct tgtgacctct    3000
ggacacataa ctcctgaact agtaagggat tataaaaacc atgcctatat cttatcagaa    3060
ttcaggtccc cccataatcc taatctcaca gcatttcatt tgtttagaaa ggccattttc    3120
agtccctgag caaggagggg gttagtttta ggataggact attatccttg cttcgttaaa    3180
ctataaacta aattcctccc atggttagct tggcctacac ctaagaatga gtgagaacag    3240
ccagcctgtg aggctagagg caagatggag tcagccatgc tagatttatc tcactgtcat    3300
aacctttgca aaggcagttt cacctgggac ataggaggta ctcaatgaaa agaagctat    3360 taatattaaa attttaaaaa tgaatttaag gaactaatac tatgtacata ttagtcatta    3420
aaacaaagtg gttcatttac attcacacaa ataaatcttg tgattataca taggtaatat    3480
gaaaaacttt gttttctttc ataatacaag gtattagcaa tagatatagt aatgttagca    3540
ttcctttgga aaaatgaaa agatttataa ttttccaaga atcattagta ttttatta     3600 atatacataa tataaaattt attcattcta taacttggaa atatgcttgc ttaccaatta    3660
ctgacagatt tcaaaatatt tctatactca caatattcat ttacataaat attgatttgg    3720
tacttacaat gtgtactgct atgctaagtt ttgtctttgt caaacatatt ttataaaatc    3780
ataatcctag atgaatccaa cttttggtaa cccacgtgcc tgaaccctg ctgttaacag     3840
```

```
gcaaagtgtg gtaggtacag atctatacct accaccttcc tctacccacc agcatctgca      3900
cccaccaccc ctccccaccc accattatct ataccaacca ccctcccaa cctaccagca       3960
tctgcaccca ccacaccgcc cacccaccac catgtacact cactacacct tccagccatc      4020
accatctgca cccatcactc ctccccatcc acaagcatct gcaccacca catttccta        4080
cctaccagca tcttcactca ccacctctcc acccaccagc atctgcaccc acaaccctc       4140
ctcacccacc agagtctgca tccatcacac ttgcccactc gctagcatct gcaccatcaa      4200
gctctgcctt cttgcctaat acgggatgag ctctccatgg ttctgcctaa agacaatgct      4260
tccactcctc ttctataacc catttccttt tacctcttca agtacacttc agaacttctc      4320
tctccttctg ataccaactt tttccacttt actcaatcat tcctatcacc atacaaacgt      4380
gtttatttct cccatcttaa agttaaaaat caaagaaaa ttgtctgcgg ccaggcacgg       4440
tggctcacgc ctgtaatccc aacactttgg gaggccaagg agggtggat gacttaaggt       4500
taggagttca agaccagcct ggccaacatg gtgaaaccca tctctactaa aaatacaaaa      4560
attagccagg catggtggca catgcctgta gtctcaggta cttgggaggc tgaggccaga      4620
gaatggcttg aacccgggag gcagaggttg cagtgagccg agattgtgcc cttgcactcc      4680
agcctgggtg acagagtgag actccatctc aaaaataaaa aataaaaata aaacaaaga      4740
aagttatttt tacccaacat ccacattaac caaatacca tttctttatt gatctttgta      4800
aaaaaaagct cttggaaaaa ttgtctatat tcactatgac ttatctcctc caaatcactt     4860
aaacacatac caatcaggtt tttgttttca tcattccaaa gtaactttta cagccaagga    4920
cagtagcgaa ctttacatcg catatgcatt gtgaagttct tgatcctcat cttacttaac    4980
ctgtcagcag tatctgacac aggtgtcact ggctcctccc tgagatgctc tctttatttg    5040
gctttgggga caccatattc tccccattcc tactttcctc aatggccctc ctcagtctcc    5100
tttgaaaga ggaaaaagaa acttcattat ctcctggatg tagtacaaac aactcaagct     5160
caacatgtgc atactgaact ccatttcctt ttcccaaact tcgacattta cagccatccc    5220
cttttcagctg atagcaagtt tatccttcca gctactcaaa ccagaatctt tagagccatc   5280
cttgacccctt ttcctcctct cacactcaac atctatccat cagaaaattt tgttggttct   5340
actttcaaaa tgcatacaga gtcagagcat gtctcattac ctccaatagc taccatacta    5400
gtctgaacaa acatcatttc tcacctgggt tattgaacaa acatcatttc tcacctgggt    5460
tattgatagc atcctaacgg gtcttcctgt ttcttggttc ccctatatta gcaacacagc    5520
agtcagagga gtccttttag aactcaatca gatcatgtca cgtcactcct ctacttaaaa    5580
tccttcaatg ggtcccatta cacaaagagt acaaaccaga gccttacac tggtctacaa     5640
gttccaacat ttgactcctg ttatctctct gacatcatat tctaatatta ctgctgttgt    5700
cctttttgctc cagtcacact gtttgattag taaatattta ttaaacaaag caatcctagt   5760
ctccaaagag atcatagttt attggaggaa acaagagcct ataaatggtt acacacagaa    5820
ggtagtgatt atggttctcc ctcacctccc atcctaaact ttgacaggtg aaactcccct    5880
ggatgttgaa ggttgaggaa tttgccaggg ttcagggtgg tgttggagga ggcagggagg    5940
aagcaaggac atttcaggca ggaagaacat tacatgcaaa gatctaaaga tatgaatcag    6000
caacatatttt atggaattac aagtaaagta gaaagttctt gctaaaacat caaaaaataa   6060
agatttgtga ttagggggcc agaatgtggg agggaaagag agatacagtt cacacttta    6120
gacaggagcc agatcatgaa atgttttctc tttgtttgtt tcttccttca cagcttttga    6180
```

-continued

```
tatgctcttg gagcaatttta ttaaccatat tttttaatgc atctcctgaa cagagtcaaa      6240
gcaatacttg gaaaggactc tgaatttcct gatttaaaga tacaaaagaa aaatctggag      6300
tcacaattaa tttgagaagg taaggagtg ggtgtgctac tgtatcaaat ttaatttgta      6360
caaaatcatc atctctagta acattatttt ttctaatcta ctgcgtttag actactttag      6420
taaagcttga tctccctgtc tatctaaaca ctgattcact tacagcaagc ttcaggctag      6480
cattggtcat attaatacccc aacaaatcca caaggtgtta gttgcacatg attttgtata      6540
aaaggtgaac tgagatttca ttcagtctac agctcttgcc aggcaaggca gccgaccaca      6600
ggtgagtctt ggcatctacc gttttcaagt gtgacagcta cttttgaaat tacagatttg      6660
tcaggacatg gaggacaaaa ctagagcttc tcactactgt tgtgtaggaa atttatgctt      6720
gtcaacctgg cttgtaaaat atggttaata taacgtaatc actgttagca agtaactgac      6780
tttatagacc aatatgcctc tcttctgaaa tggtcttatt ttaaacaaat gtgagcaaaa      6840
gaaaatattt atgagattct aaaaatgaag acataatttt gtagtataga attttcttgg      6900
ccaggaatgg tggctcatgc ttgtaatccc agcactttgg gaggccaagg tcagaggatt      6960
gcttgagcct ggaaggttga agatgcagtg attcatgatt ataccactgc actccagcct      7020
gggcaacaga gcaagaccct gtctcaagaa aagaaaagaa ttttattttt cttttcagac      7080
aaaaatagac tttaaaataa taatggaaga acaaatatga tgatcacaat tatcagagta      7140
attactttat gacagtcagc aataagattc taatctttaa atattcctct gcttaaatca      7200
ttatattgga gttttgatct ataatatatt cccaccctga cccaaaaatt gaagaaggac      7260
aaggaaaaat gttgttccaa gaaacaaaga tgtaagtaaa aaggcataag gaaggaaaaa      7320
aaacttttga agcaaaatgt gattgaggag gatgagcaga ccaattatt ttggtttggt      7380 cagcttacat aatgattatc gttctttggt ttctcagttt ctagtgggct tcattgtttg      7440
cttcccagac caggatgaag acactccagt ttttcttcct tttctgttgc tggaaagcaa      7500
tctgctgcaa tagctgtgag ctgaccaaca tcaccattgc aatagagaaa gaagaatgtc      7560
gtttctgcat aagcatcaac accacttggt gtgctggcta ctgctacacc agggtaggta      7620
cc                                                                    7622
```

<210> SEQ ID NO 2
<211> LENGTH: 6038
<212> TYPE: DNA
<213> ORGANISM: Homo sapiens

<400> SEQUENCE: 2

```
ggatccgaga acatagaagg agcaggtaat ttatcaaggc atgaacacgg gtgcttaatt        60
tcctattttg aggccaggca tggtggctca cacctgtaat cccaacactt taggaagcca       120
aggtgggtgg attgcttgag tctaggattt tgagaccagc ctggccaaca tggcgaaatc       180
ctgtctctac taaaaatact aaaattaacc agtcatggtg gtggtgtgcc tttagtccca       240
gctactctgg tggctgaggc acaagaatca cttgaacctg ggaggcagag gttgcagtga       300
gctgagactg tgccacttca ctccagcctg ggtgacagag taagattctg tctcaaaaaa       360
tatgtatata tacacacata taatagatac ataaacatat atacatatat aatatataaa       420
tatatatatt atatataata tataaacata tataaatata tatatatata tatatatata       480
tatataaacc aaacataaag gaataatttt gggggaaaat cttcataaat gaaagaacaa       540
cataggctgt tgagtatatg cacagaaatt caagagatct tccagcaatt gaagacattg       600
gtttaccaga attcacaaaa gaagtcagct gtgcatttaa agtagaatgt gatgagtgtt       660
```

-continued

```
accactgagg taggaactgg gaactaagga agcgtaagac agaaagtgct gaactgagag      720
ttgggcattg gaggctgtgt aaggcagggt aagtgaatgt ctcctagaag ctacctttaa      780
atggagtttt gaagtacttg taggagtagc ttaggtgaaa agaagaggag aaacatgtat      840
caggcagagg gactagaacc ttattacctt caaagaagaa gcaaaaagaa tacatgtgac      900
tttgaggtgg tgggaggtgc tttaagccaa tataggtgaa tttgacatag gacttcccta      960
aataatgttc ggtcatttgt taaatattga gtgatatatc actgtattaa agcccaagag     1020
ttgcttttat atagaaagaa gaaaaagcc caagagagtt ttatttctag agggaatatt      1080
ttctagaaat aaaggaaggt gtatcagcca gtttctagtc aggaaaacag aaatcacacc     1140
tgatatgcaa aatagaggaa aatcagggaa ttcattaatc cagagatttg gttgctcaag     1200
tattagattg ctgaaaagcc agacagggaa tatgaggcaa tcagagataa gtattagtga     1260
caagctccat ttatgtgcag gattggaggg acataggtgg ggttcccaga agccagaagg     1320
tgagaccacc tagcagaagc tcaaaccaca gctgggttt cctcacaaaa gctgggacca      1380
ccaggaggag ctgtccaatg ggatctggag ccagggagag catgcagtca ctaccaggaa     1440
gggaagcaga atgtaaaagg tagagagaaa tactccaact gcttccttgc attcactttc     1500
caatctccat tcacaaaggc aaaaacctgc taatacagca gagtgggaaa agcagcctgc     1560
caaggtcctt tctcccacaa aacagagcac aaaaccaagc aaaaacaagg aatgcatttg     1620
atagcaaaca ggctatggac caacccaaca taaaagaaat gatgagtgat ttcttttttc     1680
atttggttca agaaaagtat ttcagtaact attatgtaac agaaattcta tttattttgg     1740
ggaattcaaa ggtgaataaa aaagaactct aaattttat caataaaata tttcaaaaac      1800
ctcaatgaga gtaatggcat taactagcaa atatgctaat gagatgagct agccataaga     1860
ggcttagaat tgagagaaag gtctgggggc ctcttgacag gccaaattca gagctgtttg     1920
tgggaatctc tgacctaact gcaggtggaa atataaatat gggcatttag aatagtggcc     1980
caaactttgg atgatttctg tcttggggtc tctccaatta atgggattga tgagaactgt     2040
agaccactga ggtcaccatg gctcaatgaa tagtcccctg gctttggagt caaactgacc     2100
tgaatatgaa ccccagcttt gctacttaca ggttgcattt atcctcagtt ttctcatctt     2160
tcaaagaaga acagtaactt cttttaaaagg ttattgtagg ctgggtgcag tggctcacgc     2220
ctgtaatcgc agcactttgg gaggcggagg ctagtggatc acttgaggcc aggagttgga     2280
aactagcctg gccaacatgg tgaaactctg tctctacaaa aagaaattta aaaaattttg     2340
ctgggtgtgg tggcacacac ctggaattcc agctacctgg gaggccgagg catgagcatc     2400
acttgagtct ggaaagcaga gggttgcagt gagccaagat tgtaccactg tactcaagcc     2460
tgggtgacac agtgagacct tgtctaaaaa aaaaaaaggt tattgtgtta ttgtaaatat     2520
tgtatatgaa cttctattta acatgtttag ttaaatgcct gtgtaattgt ccaatgtgct     2580
cttctagctc actgcacaga caaaactgat tcactgaaat catggaattg cagcaaagaa     2640
caaatctaat taatgtaggt caaacgggag gactggagtt attattcaaa tcagtctccc     2700
tgaaaactca gaggctaggg ttttatggat aatttggtgg gcaggggact agggaatggg     2760
tgctgctgat tggttgggga atgaaatagt aagattgtga aaaactgtcc tccttcattg     2820
agtctgcttc cgggtgtagg ccacacgacc agttgagtca tgaagcatgc gtccaagtgg     2880
agtcagtttt ttgccagaat gcaaaagcct gaaaaatgtc tcaaatgatc aactgtaggc     2940
tccacaataa tgatattatc tataggagca attggggaag taacaaatct tgtgacctct    3000
```

```
ggacacataa ctcctgaact agtaagggat tataaaaacc atgcctatat cttatcagaa    3060
ttcaggtccc cccataatcc taatctcaca gcatttcatt tgtttagaaa ggccattttc    3120
agtccctgag caaggagggg gttagtttta ggataggact attatccttg cttcgttaaa    3180
ctataaacta aattcctccc atggttagct tggcctacac ctaagaatga gtgagaacag    3240
ccagcctgtg aggctagagg caagatggag tcagccatgc tagatttatc tcactgtcat    3300
aacctttgca aaggcagttt cacctgggac ataggaggta ctcaatgaaa agaagctat     3360 taatattaaa attttaaaaa tgaatttaag gaactaatac tatgtacata ttagtcatta    3420
aaacaaagtg gttcatttac attcacacaa ataaatcttg tgattataca taggtaatat    3480
gaaaaacttt gttttctttc ataatacaag gtattagcaa tagatatagt aatgttagca    3540
ttcctttgga aaaaatgaaa agatttataa ttttccaaga atcattagta tttttattta    3600
atatacataa tataaaattt attcattcta taacttggaa atatgcttgc ttaccaatta    3660
ctgacagatt tcaaaatatt tctatactca caatattcat ttacataaat attgatttgg    3720
tacttacaat gtgtactgct atgctaagtt ttgtctttgt caaacatatt ttataaaatc    3780
ataatcctag atgaatccaa cttttggtaa cccacgtgcc tgaaccoctg ctgttaacag    3840 gcaaagtgtg gtaggtacag atctatacct accaccttcc tctacccacc agcatctgca    3900
cccaccaccc ctccccaccc accattatct ataccaacca cccctcccaa cctaccagca    3960
tctgcaccca ccacaccgcc cacccaccac catgtacact cactacacct tccagccatc    4020
accatctgca cccatcactc ctccccatcc acaagcatct gcacccacca catttcccta    4080
cctaccagca tcttcactca ccacctctcc acccaccagc atctgcaccc acaacccctc    4140
ctcacccacc agagtctgca tccatcacac ttgcccactc gctagcatct gcaccatcaa    4200
gctctgcctt cttgcctaat acgggatgag ctctccatgg ttctgcctaa agacaatgct    4260
tccactcctc ttctataacc catttccttt tacctcttca agtacacttc agaacttctc    4320
tctccttctg ataccaactt tttccacttt actcaatcat tcctatcacc atacaaacgt    4380
gtttatttct cccatcttaa agttaaaaat caaagaaaa ttgtctgcgg ccaggcacgg    4440
tggctcacgc ctgtaatccc aacactttgg gaggccaagg agggttggat gacttaaggt    4500
taggagttca agaccagcct ggccaacatg gtgaaaccca tctctactaa aaatacaaaa    4560
attagccagg catggtggca catgcctgta gtctcaggta cttgggaggc tgaggccaga    4620
gaatggcttg aacccgggag gcagaggttg cagtgagccg agattgtgcc cttgcactcc    4680
agcctgggtg acagagtgag actccatctc aaaaataaaa aataaaaata aaacaaaaga    4740
aagttatttt tacccaacat ccacattaac caaataccca tttctttatt gatctttgta    4800 aaaaaagct cttggaaaaa ttgtctatat tcactatgac ttatctcctc caaatcactt    4860
aaacacatac caatcaggtt tttgttttca tcattccaaa gtaactttta cagccaagga    4920
cagtagcgaa ctttacatcg catatgcatt gtgaagttct tgatcctcat cttacttaac    4980
ctgtcagcag tatctgacac aggtgtcact ggctcctccc tgagatgctc tctttatttg    5040
gctttgggga caccatattc tccccattcc tactttcctc aatggccctc ctcagtctcc    5100
tttggaaaga ggaaaaagaa acttcattat ctcctggatg tagtacaaac aactcaagct    5160
caacatgtgc atactgaact ccatttcctt ttcccaaact tcgacattta cagccatccc    5220
ctttcagctg atagcaagtt tatccttcca gctactcaaa ccagaatctt tagagccatc    5280 cttgacccctt ttcctcctct cacactcaac atctatccat cagaaaattt tgttggttct    5340
actttcaaaa tgcatacaga gtcagagcat gtctcattac ctccaatagc taccatacta    5400
```

-continued

```
gtctgaacaa acatcatttc tcacctgggt tattgaacaa acatcatttc tcacctgggt      5460
tattgatagc atcctaacgg gtcttcctgt ttcttggttc ccctatatta gcaacacagc      5520
agtcagagga gtccttttag aactcaatca gatcatgtca cgtcactcct ctacttaaaa      5580
tccttcaatg ggtcccatta cacaaagagt acaaaccaga gccttacac tggtctacaa       5640 gttccaacat ttgactcctg ttatctctct gacatcatat tctaatatta ctgctgttgt      5700 cctttttgctc cagtcacact gtttgattag taaatattta ttaaacaaag caatcctagt     5760
ctccaaagag atcatagttt attggaggaa acaagagcct ataaatggtt acacacagaa      5820
ggtagtgatt atggttctcc ctcacctccc atcctaaact ttgacaggtg aaactcccct      5880
ggatgttgaa ggttgaggaa tttgccaggg ttcagggtgg tgttggagga ggcagggagg      5940
aagcaaggac atttcaggca ggaagaacat tacatgcaaa gatctaaaga tatgaatcag      6000
caacatattt atggaattac aagtaaagta gaaagttc                              6038
```

<210> SEQ ID NO 3
<211> LENGTH: 542
<212> TYPE: DNA
<213> ORGANISM: Homo sapiens

<400> SEQUENCE: 3

```
tcactgttag caagtaactg actttataga ccaatatgcc tctcttctga aatggtctta      60
ttttaaacaa atgtgagcaa agaaaaatat ttatgagatt ctaaaaatga agacataatt      120
ttgtagtata gaatttttctt ggccaggaat ggtggctcat gcttgtaatc ccagcacttt     180
gggaggccaa ggtcagagga ttgcttgagc ctggaaggtt gaagatgcag tgattcatga     240
ttataccact gcactccagc ctgggcaaca gagcaagacc ctgtctcaag aaaagaaaag     300 aatttttattt ttcttttcag acaaaaatag actttaaaat aataatggaa gaacaaatat     360
gatgatcaca attatcagag taattacttt atgacagtca gcaataagat tctaatctttt     420 aaatattcct ctgcttaaat cattatattg gagttttgat ctataatata ttcccaccct     480
gacccaaaaa ttgaagaagg acaaggaaaa atgttgttcc aagaaacaaa gatgtaagta    540
aa                                                                     542
```

<210> SEQ ID NO 4
<211> LENGTH: 3213
<212> TYPE: DNA
<213> ORGANISM: Homo sapiens

<400> SEQUENCE: 4

```
actaacataa agctgaaggt gaataaaaaa atcagggtta gccaaacaaa ttttcatggt      60
caaataccac ataaaaagta aatatactta agttcccagc aaaatctgaa ttgaacgtag     120
acaaaatgct catttctcag tgtttgacag acttaacagt ttgagccaat aaaaatgtac     180
tgactagata aactactaaa agttgttaat ttttgcaatg tatatttctg aaaagaaagt     240
ttatctatta tagaaattcc tgtgcccatt taagaacttt gagcatttta attgtttaat     300
aatatagttt aattgcatca tgaaaataat caataataca atttatttgg tttatttaaa     360
aaaactgatt ctttctgctc tctctatata tagactgatt ttatactaat gttgcctaaa     420
gatcaccaaa ttgtttgaag cctaggtttc tgagggatgg aaaatgatgt cacaactatt      480
tacagttcac acacacattc tggggattta atacatcctt tacaagtgca ggaaaggtgg     540
aagattgatg atttggggga attagagcta ccacacccca gagggtggta tggtatgttg     600
```

-continued

```
tctgttgtga gctgtgtgaa tcagagagtt tgatttagac atatatttag aaagaggaaa    660
gatgaaccaa tcaaaaataa taactataat gacttttcaa gatatagaca atacagttaa    720
gatataaatg gaaacaaaaa aagttaaaag tggggagatg aagtctgatt ttttggtttt    780
tttttttttt tgctttttg tttgtttatg taatcagtgt taccagttta aataatggg     840
ttataagaca ctatatgcaa gcctcatggt aacctccaat ctaaaacata caacaaatac    900
acacaaaata aaaaggagaa attaaaacac accaccagag aaaatcacct acattaaaag    960
aaagacaaat aggaagaaaa taagaaagag aaggccatca ataatcaga aaatgaataa   1020
caaaatgaca ggaataagtc ctcataaata ataacattga atgtaaatgg actaagctct  1080
ccaatgaaag acagggagtg gctgaatgta ttttaaaaaa aatattacac cgagctgtgc  1140
gtggtgtctc acacctataa tcccagcatt ttgggagact gagccgggtg gatcacttga  1200
gcccaggagt tcgagaccag cctggccaac atggcaaaac cctgtctcta ctaaaaatac  1260
aaaaaattag ctgaacatgg tggcacatgc ctgtggttcc agctactaga gaggctgagg  1320
cagaagaatt gcttgaactt gggaggtgga ggttgcagtg agctaagatt gatgagcca   1380
ctgcacccca gcctaggtga cagaataaga ctctgcctca aaaaaaaaa gcaaacaaa    1440
acaaaacaaa aaacccttag acccaatgat tcattgccta caagaagtat gcttcacctt  1500
taaagacaca tatagactga aggtaaaggg atggaaaaat attctatgcc tatgaaaca   1560
aacaaaaaga agcagaagct acatttatat cagacaaaat agactgcaag acaaaaacta  1620
tgaaaagaga gaaagaaggt cattatatag tgataaaggg gtccatttag caagagcatt  1680
taacaattct aaatatatat tcacccaata ctggagtact caggtatata aagcaaaatat 1740
tattagagcc aaagagagag atagacagac ccccatacaa taataactgg agacttcaac  1800
acccccacttt cagcattgga cagatcatcc agacagaaaa ttaacaaaca tcaaatttca  1860
tctgcaccat aggtcaaatg gacctagtag atatttacag aacatttgat ccaacagctg  1920
tagaatacac attcttctcc tcagcacatg gataattctc aaggatatac caaatgctag  1980
gtcacaaaac aaatcttaaa atttagaaaa aaagtgaaat aatatcaaac gttttctctc  2040
accacagact aagaaaaaaa gaagtcccaa ataaatacaa tctgagataa aaaggagac   2100
gagacaacca ataccacaaa aaattaaagg atcattagaa gatactatga aactatatgc  2160
taataaattg gaaaacctga acaaaataga taattcctag aaacatacaa catactggtc  2220
tgttcaggtt ttgtattttt tcatagtacc atgaagaaat acaagaattg tttctagaac  2280
cattcttgta tttcttcatg gttttttgtat ttcttcatgg aaccatgaag aaatacaaaa 2340
tgtgaacagg ccaataacaa gtaatgagac agaagccata ctaaaaagta tcccagaaaa  2400
gaactcagga tctgatggct tcactgatga attttgccaa atatttaaaa aactaatacc  2460
aatccaactc aaattattaa aaaatagag gtggacagaa tctttccaaa tgtattctat  2520
gaggccagtg ttttttctga ttgaatctcc cattatattt taatcacata taaaaccaga  2580
gaaagacaca ttaaaagaa agaaaactgt aggccaatat ctctgatgaa cattgatgca  2640
gaaatcctca acaacaaatt agcaaactga attcaagaac acattaaaac aatcattcat  2700
catgaccaag tggaatttgt cctagagatt caagtgtggt taggtatgtg cagatcaatg  2760
ggtttaatgt tgtccaatga acataatgtc ctccagctcc atccatgttc ttgcaaatga  2820
caggatctca ttcttttttta tggctaagta gtactccatt gtgtataagt gccatatttt  2880
ctttatccat tcatctgtta gacacctaag ttgcttccaa atcttagcta ttgtgaatag  2940
tgctgcaata acatgggag tgtaaatatt ttgttgacat actgatttca tttccttttgg  3000
```

-continued

```
ataaataccc agtagtggga ttgctggatc atatggggga aaatggagat ggctaacggg   3060
ctcaaaaata tagttagaaa aaatgaatat gatttagtat tcgatagcac aataggatga   3120
ctactgttaa tgataatttta ttatatatta taaaataact aaaatagtat aaatgggatg   3180
tatgtagcag agagaaatga taaatgtttg aag                                3213
```

<210> SEQ ID NO 5
<211> LENGTH: 6679
<212> TYPE: DNA
<213> ORGANISM: Homo sapiens

<400> SEQUENCE: 5

```
gtcgacctgc aggtcaacgg atcacttgag gacagtagtt caagaccagc ctgggcagca     60
tagggagact gtctctacga aaaatcaaaa aattatggcc gggcatggtg gctcacgtct    120
gtaatccctg aactttggga catcaaggca agtggatcac ttgaggtcag gagttcgaga    180
ctagcctggc caacatggtg aaaccctatc tccactaaaa aatacaaaaa ttagccaggc    240
atggtggcag gcacctgtaa tcccggctac tcaggaggct gaggcaggag aatcacttga    300
acccaggagg cggaggttgc agtgagctga gatcacacca ctgcactcca gcctgggtga    360
cagagcaaga ctctatctca aaaaaataa aaaaataaaa aaattagcca ggcatggtag    420
tgcacacctc tagtctcagc tactcaggag gctgaggtgg gaggatcact tgaacctggg    480
gcagtcaagg ctacagtgag ccaagatcat gccactacac tccagcctgg gcaacagaga    540
gagaccctgt ctctaaaaaa ataataataa taaagaaaaa aacagctctg tttatgtctc    600
ctggtccata catactacta tgtatatagt ttgcaaactc aaagatccag atagtcaatt    660
ttttaggctt gtgggccgta tggtctctgt cacaatcact ctgccctgtc tttctagcac    720
aaaagcagct ataaacaata catacatgaa ttttttatag acatcgagat ttgaatttca    780
tatgattttt acattttata aaataatctt tttaaaaatt ttcccctaac catttaaaag    840
tgtaaaagcc ggccagcgcg ccatcgtcac gcctgtaatt ccagcacttt gggaggctga    900
ggtgggcaga tcacttgaga tcaacagttc gagaccagcc tggccaacat agcaaaaccc    960
catttctact aaaaataaaa aaattagctg ggcatagtgg tgcacacctg tgatcccagc   1020
tacttgggag gctgaggcag gagaatcgct tgaacctggg aagcggaggt tgcagtgagc   1080
caacatcatg ccactgcact ccagcctggg tgacagagtg agacttcgtc tcaacgaaaa   1140
aaaaaagtgt aaaagccatt cctaattcag tgtacatcag tgtacatact caggtctgcg   1200
tactcctgct ctgaggcata cctgagaagt agagttgctt ggtcacagga catacacatt   1260
tccacattaa ctagacacta ccaagttgcc atccaaggag gtttttttt tacaatctac   1320 actccccca gcaacaaatg agagttactc cagatccttt acaaagatgc tctaagccca   1380
gtaccagatg aaaacaggaa gtgggagggg aagctgccag ccccttctaa ccatgaagaa   1440
atacctggta gagccttctg gatgctggaa ggatgaataa cggggtctc tggagcctgc   1500 cccctgtcag atcactgtga cttctgagcc tccagtccga tctcagcccc atgtgtcatg   1560
gccagtgata atgagccctc actctctgtt tggtctttat tctccccatg tggggctgaa   1620
gtctggattg agccgttatt caagatgtac agctttcttg acaggaaagt agtgtcacag   1680
aaacagcagg ggcttggcaa gatgatctaa ctgcaaatcc tacctggctc agccaccagc   1740
tagttctgtg atcttgaaca gtttttttca cttctctgag gccatccctt ggctacaaca   1800
caccagttgg ttgacaggat gaaatgacga agtcccttac acctgtaatc ccagcacttt   1860
```

-continued

```
gggaggccaa ggcgggtgga tggcttgagc ctgagaggtg acagcatgcc ggcagtcctc      1920
acagccctcg ttcgctctcg gcgcctcctc tgcctgggct cccacttcgg tggcacttga      1980
ggagcccttc agcccaccgc tgcactgtgg gagccccttt ctgggctggc caaggccaga      2040
gccggctccc tcagcttgca gggaggtgtg gagggagagg ctcaagcagg aaccggggct      2100
gcgcacggcg cttgcgggcc agctggagtt ccgggtgggc gtgggcttgg cgggccccgc      2160
actcggagca gcgggccagc cctgccaggc cccgggcaat gagaggctta gcacccgggc      2220
cagcggctgc ggagggtgta ctgggtgccc cagcagtgcc agcccgccgg cgctgtgctc      2280
gctcgatttc tcactgggcc ttagcagcct tcccgcgggg cagggctcgg gacctgcagc      2340
ccgccatgcc tgagcctccc ctccatgggc tcctgtgcgg cccgagcctc cccgacgagc      2400 accacccct gctccacagc gcccagtccc atcgaccacg caagggctga gaagtgcggg       2460
cgcacggcac cgggactggc aggcagctac ccctgcagcc ctggtgcgga atccactggg      2520
tgaagccagc tgggctcctg agtctggtgg agacttggag aacctttatg tctagctcag      2580
ggatcgtaaa taccaatc agcaccctgt gtctagctca gggtctgtga atgcaccaat       2640
ccacactctg tatctagcta ctctgatggg gccttggaga acctttatgt ctagctcagg     2700
gattgtaaat acaccaatcg gcactctgta tctagctcaa ggtttgtaaa cacaccaatc     2760
agcaccctgt gtctagctca gggtatgtga atgcaccaat cgacagtctg tatctggcta     2820
ctttcatggg catccgtgtg aagagaccac caaacaggct ttgtgtgagc aataaagctt     2880
ctatcacctg ggtgcaggtg ggctgagtcc gaaaagagag tcagcgaagg gagataaggg     2940
tggggccgtt ttataggatt tgggtaggta aaggaaaatt acagtcaaag ggggtttgtt     3000
ctctggcggg caggagtggg gggtcgcaag gtgctcagtg ggggtgcttt ttgagccagg     3060
atgagccagg aaaaggactt tcacaaggta atgtcatcaa ttaaggcaag gacccgccat     3120
ttacacctct tttgtggtgg aatgtcatca gttaagttgg ggcagggcat attcacttct     3180
tttgtgattc ttcagttact tcaggccatc tgggcgtata tgtgcaagtt acaggggatg     3240
cgatggcttg gcttgggctc agaggcttga cagctactct ggtggggcct tggagaatgt     3300
ttgtgtcgac actctgtatc tagttaatct agtggggacg tggagaacct ttgtgtctag     3360
ctcagggatt gtaaacgcac caatcagcgc cctgtcaaaa cagaccactc ggctctacca     3420
atcagcagga tgtgggtggg gccagataag agaataaaag caggctgccc gagccagcag     3480
tggcaacgcg cacaggtccc tatccacaat atggcagctt tgttcttttg ctgtttgcga     3540
taaatcttgc tactgctcgc ttttttgggtc cacactgctt ttatgagctg taacactcac     3600
cacgaaggtc tgcagcttca ctcctgaagc cactaagacc acgagcccac cgggaggaat     3660
gaacaactcc ggccgcgctg ccttaagagc tataacactc accgcgaagg tctgcagctt     3720
cactcctcag ccagcgagac cacgaaccca ccagaaggaa gaaactgcga acacatctga     3780
acatcagaag gaacaaactc cagatgcacc accttaagag ctgtaacact cactgcgagg     3840
gtccgcggct tccttcttga agtcagtgag accaagcact caccagtttc ggacacaagc     3900
ccaggagttt gagatcagcc tggcaacat gatgaaatgc cctctctgca aaaaaaaaa       3960 aaattacaaa aattggcgga gcatggtggt ccgtgcctgt ggtcccagct acgcgggagg     4020
ctaaagtggg aggatcgctt gagcctggga ggtgaagact gcagtgagct gtgattgtac     4080
cacagccctc taggctgggg gacagactga gaccctgttt cccctccgca aaaaattga      4140 caaaagtgta ataagaggtg cctgatatgg ctaggcgcag tggctcatgc ctgtaatccc     4200
agcactttgg gaagccgagg cgggcgggtc acctaaggtc aggagtgtga ccagcctg       4260
```

```
gccaacatgg agaaagccca tctcttctaa aaatacaaaa ttagccggct gtgggggcag    4320
tggtggagca tgcctgtaat cccagctact caggaggctg aggcaggaga atcacttgaa    4380
cccaggaggc ggcggttgca gtgagccgag atcgtgccat tgcactccac ccactccagc    4440
ctgggcaaca agagcaaac tctgtcttaa aaaaaaaaa aaaaagtgcc tgacatataa     4500
gaggtgtgca atgcaatagt tgccaggcaa catgtttaag aatgtggagc tcctgccttc    4560
catggtcctg ttaaaaaccc accctcaagg ccaggtgcag tggctcatgc ctataatccc    4620
agcactttgg gaggccgagg cgggtggatc acctgaggtc aggagttcga gaccagcctg    4680
accaccaaca tggtgaaatc ccacctctac taaaaataca aaattagatg agcatggtgg    4740
tgcatgcctg taatcccacc tacttgggag gctgaggcag gaaaatcact gaaccaggg    4800 aggcggaggt tgtagtgagc cgagatcgtg ccattgcact ccagcctgag caatgagcga    4860
aactccatct caaaaaaaca acaacaaaaa cccactctct actcccaggg agctgggtac    4920
agagctgggc cacatcagtg caaggtgctg agccacagag ctaaggcgga gctgcaggac    4980
cgcggaccag ataacagtgt gtgagatcag tgtgtgagat cagacgtccc tgccattggt    5040
gaccaccagg gggcccccaa gcaccagaga tggccccatc cagtcaccac atccacttct    5100
catccagaga tgtctgtttc ttggcacgct ggggtaaatt aggacagaag gtgacagtct    5160
tgggtgtggt cagtcagact gccccaggca ggccttgtgg cctgtagaaa cgttcaggc    5220 ctaggccggg cacggtggct cacgcctgta atcccagcac tttgggaggc cgaggcgggt    5280
ggatcacgag gtcaggagat cgtgaccatc ctggctaaca cggtgaaacc ccgtctctac    5340
taaaaataca aaaaattggc cgggcatggt ggcgggcacc tgtagttcca gctactcggg    5400
aggctgaggc aggagaatgg cgtgaacccg agaggcagag tttgcagtga gccgagatcg    5460
cgccactgca ctccagcctg gcgacagag caagactcca tctggaaaag aaaaagaaaa    5520
cgttcaggtc tgagccagag gcccaggctg taattctgtc acttaccatg accttgggca    5580
aggcacttcc ttccctggcc cagttcacgg ggttggaatc gactccaagg tcccttccag    5640
cattaacgct gcatggttct aagatgagaa gatggggcag tttcccctct ctcacccag    5700 cccgtgtcca cttcaaggtg aatgaccagg gaagtcacgt gtcccaatcc cgcagttcca    5760
aagcccttgg ggaccctact gtcagggtcg tgcacgagga ggtgaaggtc aggtgagcca    5820
atcgcctcga agggtcttgc ctcattcggg acagacatcc ggtttcctct ggctctaccg    5880
ggattctagg ggctttagcc gaatgagtca tgggggcggcg ggggtttct ggggagttc    5940 ccagctaatc aacttgggac aggacagcct ggaactttcg atggtgccta tccaagtgtg    6000
gggtgggcac agcagccaag acccaatgtc cttatctcag gtaggggctc aggaggtctc    6060
ccagacaggc agcctccgga gagtttgggg gtaggaatgg gagcaaccag gcttcttttt    6120
ttctctctta gaatttgggg gcttgggga caggcttgag aatcccaaag gagaggggca    6180
aaggacactc ccccacaagt ctgccagagc gagagaggga accccgact cagctgccac    6240 ttcccccacag gcctctgccg cttccaggcg tctatcagcg gctcagcctt tgttcagctg    6300
ttctgttcaa acactctggg gccattcagg cctggtggg gcagcgggag gaaggggagtt    6360 tgagggggc aaggcgacgt caaggagga tcagagattc cacaattcca caaactttc    6420 gcaaacagct ttttgttcca accccctgc attgtcttgg acaccaaatt tgcataaatc    6480 ctggaagtt attactaagc cttagtcgtg gcccaggta atttcctccc aggcctccat    6540
ggggttatgt ataaagggcc cctagagct gggccccaaa acagcccgga gcctgcagcc    6600
```

| | |
|---|---:|
| cagcccacc cagacccatg gctggacctg ccacccagag ccccatgaag ctgatgggtg | 6660 |
| agtgtcttgg cccaggatg | 6679 |

<210> SEQ ID NO 6
<211> LENGTH: 6235
<212> TYPE: DNA
<213> ORGANISM: Homo sapiens

<400> SEQUENCE: 6

| | |
|---|---:|
| gatcacttga ggacagtagt tcaagaccag cctgggcagc atagggagac tgtctctacg | 60 |
| aaaaatcaaa aaattatggc cgggcatggt ggctcacgtc tgtaatccct gaactttggg | 120 |
| acatcaaggc aagtggatca cttgaggtca ggagttcgag actagcctgg ccaacatggt | 180 |
| gaaaccctat ctccactaaa aaatacaaaa attagccagg catggtggca ggcacctgta | 240 |
| atcccggcta ctcaggaggc tgaggcagga gaatcacttg aacccaggag gcggaggttg | 300 |
| cagtgagctg agatcacacc actgcactcc agcctgggtg acagagcaag actctatctc | 360 |
| aaaaaaaata aaaaaataaa aaattagcc aggcatggta gtgcacacct ctagtctcag | 420 |
| ctactcagga ggctgaggtg ggaggatcac ttgaacctgg ggcagtcaag gctacagtga | 480 |
| gccaagatca tgccactaca ctccagcctg ggcaacagag agagacctg tctctaaaaa | 540 |
| aataataata ataaagaaaa aaacagctct gtttatgtct cctggtccat acatactact | 600 |
| atgtatatag tttgcaaact caaagatcca gatagtcaat ttttaggct tgtgggccgt | 660 |
| atggtctctg tcacaatcac tctgccctgt ctttctagca caaagcagc tataaacaat | 720 |
| acatacatga attttttata gacatcgaga tttgaatttc atatgatttt tacatttat | 780 |
| aaaataatct tttaaaaat tttcccctaa ccatttaaaa gtgtaaaagc cggccagcgc | 840 |
| gccatcgtca cgcctgtaat tccagcactt tgggaggctg aggtgggcag atcacttgag | 900 |
| atcaacagtt cgagaccagc ctggccaaca tagcaaaacc ccatttctac taaaaataaa | 960 |
| aaaattagct gggcatagtg gtgcacacct gtgatcccag ctacttggga ggctgaggca | 1020 |
| ggagaatcgc ttgaacctgg gaagcggagg ttgcagtgag ccaacatcat gccactgcac | 1080 |
| tccagcctgg gtgacagagt gagacttcgt ctcaacgaaa aaaaaaagtg taaaagccat | 1140 |
| tcctaattca gtgtacatca gtgtacatac tcaggtctgc gtactcctgc tctgaggcat | 1200 |
| acctgagaag tagagttgct tggtcacagg acatacacat ttccacatta actagacact | 1260 |
| accaagttgc catccaagga ggttttttttt ttacaatcta cactcccccc agcaacaaat | 1320 |
| gagagttact ccagatcctt tacaaagatg ctctaagccc agtaccagat gaaaacagga | 1380 |
| agtgggaggg gaagctgcca gcccttcta accatgaaga aatacctggt agagccttct | 1440 |
| ggatgctgga aggatgaata acgggggtct ctggagcctg cccctgtca gatcactgtg | 1500 |
| acttctgagc ctccagtcca gtctcagccc catgtgtcat ggccagtgat aatgagccct | 1560 |
| cactctctgt ttggtctta ttctccccat gtggggctga agtctggatt gagccgttat | 1620 |
| tcaagatgta cagcttctt gacaggaaag tagtgtcaca gaaacagcag gggcttggca | 1680 |
| agatgatcta actgcaaatc ctacctggct cagccaccag ctagttctgt gatcttgaac | 1740 |
| aagttttttc acttctctga ggccatccct tggctacaac acaccagttg gttgacagga | 1800 |
| tgaaatgacg aagtccctta cacctgtaat cccagcactt tgggaggcca aggcgggtgg | 1860 |
| atggcttgag cctgagaggt gacagcatgc cggcagtcct cacagccctc gttcgctctc | 1920 |
| ggcgcctcct ctgcctgggc tcccacttcg gtggcacttg aggagccctt cagcccaccg | 1980 |
| ctgcactgtg ggagcccctt tctgggctgg ccaaggccag agccggctcc ctcagcttgc | 2040 |

```
agggaggtgt ggagggagag gctcaagcag gaaccggggc tgcgcacggc gcttgcgggc    2100
cagctggagt tccgggtggg cgtgggcttg gcgggccccg cactcggagc agcgggccag    2160
ccctgccagg ccccgggcaa tgagaggctt agcacccggg ccagcggctg cggagggtgt    2220
actgggtgcc ccagcagtgc cagcccgccg gcgctgtgct cgctcgattt ctcactgggc    2280
cttagcagcc ttcccgcggg gcagggctcg ggacctgcag cccgccatgc ctgagcctcc    2340
cctccatggg ctcctgtgcg gcccgagcct ccccgacgag caccacccc tgctccacag     2400 cgcccagtcc catcgaccac gcaagggctg agaagtgcgg gcgcacggca ccgggactgg    2460
caggcagcta cccctgcagc cctggtgcgg aatccactgg gtgaagccag ctgggctcct    2520
gagtctggtg gagacttgga gaacctttat gtctagctca gggatcgtaa atacaccaat    2580
cagcaccctg tgtctagctc agggtctgtg aatgcaccaa tccacactct gtatctagct    2640
actctgatgg ggccttggag aacctttatg tctagctcag ggattgtaaa tacaccaatc    2700
ggcactctgt atctagctca aggtttgtaa acaccaat cagcaccctg tgtctagctc       2760
agggtatgtg aatgcaccaa tcgacagtct gtatctggct actttcatgg gcatccgtgt    2820
gaagagacca ccaaacaggc tttgtgtgag caataaagct tctatcacct gggtgcaggt    2880
gggctgagtc cgaaaagaga gtcagcgaag ggagataagg gtggggccgt tttataggat    2940
ttgggtaggt aaaggaaaat tacagtcaaa ggggtttgt tctctggcgg gcaggagtgg     3000 gggtcgcaa ggtgctcagt gggggtgctt tttgagccag gatgagccag gaaaaggact     3060
ttcacaaggt aatgtcatca attaaggcaa ggacccgcca tttacacctc ttttgtggtg    3120
gaatgtcatc agttaagttg gggcagggca tattcacttc ttttgtgatt cttcagttac    3180
ttcaggccat ctgggcgtat atgtgcaagt tacagggggat gcgatggctt ggcttgggct   3240
cagaggcttg acagctactc tggtgggcc ttggagaatg tttgtgtcga cactctgtat     3300
ctagttaatc tagtggggac gtggagaacc tttgtgtcta gctcagggat tgtaaacgca    3360
ccaatcagcg ccctgtcaaa acagaccact cggctctacc aatcagcagg atgtgggtgg    3420
ggccagataa gagaataaaa gcaggctgcc cgagccagca gtggcaacgc gcacaggtcc    3480
ctatccacaa tatggcagct ttgttctttt gctgtttgcg ataaatcttg ctactgctcg    3540
ctttttgggt ccacactgct tttatgagct gtaacactca ccacgaaggt ctgcagcttc    3600
actcctgaag ccactaagac cacgagccca ccgggaggaa tgaacaactc cggccgcgct    3660
gccttaagag ctataacact caccgcgaag gtctgcagct tcactcctca gccagcgaga    3720
ccacgaaccc accagaagga gaaactgcg aacacatctg aacatcagaa ggaacaaact     3780
ccagatgcac caccttaaga gctgtaacac tcactgcgag ggtccgcggc ttccttcttg    3840
aagtcagtga gaccaagcac tcaccagttt cggacacaag cccaggagtt tgagatcagc    3900
ctgggcaaca tgatgaaatg ccctctctgc aaaaaaaaaa aaattacaa aaattggcgg     3960 agcatggtgg tccgtgcctg tggtcccagc tacgcgggag gctaaagtgg gaggatcgct    4020
tgagcctggg aggtgaagac tgcagtgagc tgtgattgta ccacagccct ctaggctggg    4080
ggacagactg agaccctgtt tcccctccgc aaaaaaattg acaaaagtgt aataagaggt    4140
gcctgatatg gctaggcgca gtggctcatg cctgtaatcc cagcactttg ggaagccgag    4200
gcgggcgggt cacctaaggt caggagtgtg agaccagcct ggccaacatg gagaaagccc    4260
atctcttcta aaaatacaaa attagccggc tgtggggca gtggtggagc atgcctgtaa     4320
tcccagctac tcaggaggct gaggcaggag aatcacttga acccaggagg cggcggttgc    4380
```

```
agtgagccga gatcgtgcca ttgcactcca cccactccag cctgggcaac aagagccaaa    4440
ctctgtctta aaaaaaaaa aaaaaagtgc ctgacatata agaggtgtgc aatgcaatag    4500
ttgccaggca acatgtttaa gaatgtggag ctcctgcctt ccatggtcct gttaaaaacc    4560
caccctcaag gccaggtgca gtggctcatg cctataatcc cagcactttg ggaggccgag    4620
gcgggtggat cacctgaggt caggagttcg agaccagcct gaccaccaac atggtgaaat    4680
cccacctcta ctaaaaatac aaaattagat gagcatggtg gtgcatgcct gtaatcccac    4740
ctacttggga ggctgaggca ggaaaatcac tagaaccagg gaggcggagg ttgtagtgag    4800
ccgagatcgt gccattgcac tccagcctga gcaatgagcg aaactccatc tcaaaaaaac    4860
aacaacaaaa acccactctc tactcccagg gagctgggta cagagctggg ccacatcagt    4920
gcaaggtgct gagccacaga gctaaggcgg agctgcagga ccgcggacca gataacagtg    4980
tgtgagatca gtgtgtgaga tcagacgtcc ctgccattgg tgaccaccag ggggccccca    5040
agcaccagag atggccccat ccagtcacca catccacttc tcatccagag atgtctgttt    5100
cttggcacgc tggggtaaat taggacagaa ggtgacagtc ttgggtgtgg tcagtcagac    5160
tgccccaggc aggccttgtg gcctgtagaa aacgttcagg cctaggccgg gcacggtggc    5220
tcacgcctgt aatcccagca ctttgggagg ccgaggcggg tggatcacga ggtcaggaga    5280
tcgtgaccat cctggctaac acggtgaaac cccgtctcta ctaaaaatac aaaaaattgg    5340
ccgggcatgg tggcgggcac ctgtagttcc agctactcgg gaggctgagg caggagaatg    5400
gcgtgaaccc gagaggcaga gtttgcagtg agccgagatc gcgccactgc actccagcct    5460
gggcgacaga gcaagactcc atctggaaaa gaaaagaaa acgttcaggt ctgagccaga    5520
ggcccaggct gtaattctgt cacttaccat gaccttgggc aaggcacttc cttccctggc    5580
ccagttcacg gggttggaat cgactccaag gtcccttcca gcattaacgc tgcatggttc    5640
taagatgaga agatggggca gtttcccctc tctcacccca gcccgtgtcc acttcaaggt    5700
gaatgaccag ggaagtcacg tgtcccaatc ccgcagttcc aaagcccttg gggaccctac    5760
tgtcagggtc gtgcacgagg aggtgaaggt caggtgagcc aatcgcctcg aagggtcttg    5820
cctcattcgg gacagacatc cggtttcctc tggctctacc gggattctag ggctttagc    5880 cgaatgagtc atgggggggcg gggggggtttc tgggggagtt cccagctaat caacttggga    5940
caggacagcc tggaactttc gatggtgcct atccaagtgt ggggtgggca cagcagccaa    6000
gacccaatgt cctttatctca ggtaggggct caggaggtct cccagacagg cagcctccgg    6060
agagtttggg ggtaggaatg ggagcaacca ggcttctttt tttctctctt agaatttggg    6120
ggcttggggg acaggcttga gaatcccaaa ggagaggggc aaaggacact cccccacaag    6180
tctgccagag cgagagaggg agacccctgac tcagctgcca cttccccaca ggcct        6235
```

<210> SEQ ID NO 7
<211> LENGTH: 278
<212> TYPE: DNA
<213> ORGANISM: Homo sapiens

<400> SEQUENCE: 7

```
aagcttttat aggtgtaaat tttccactta gtactgcttt tgtaatgttg tcttttatt      60 ttcatttatc tcaagatgtt ttctaatttc tcttgacttc cttcttaaat tcttacctca    120
tgtagacata cattttggc cctatgcatt gggatgcaaa accagactaa tttactttgt     180
acaaaaagaa aaatgagaaa gaaatatatt tggtcttgtg agcactatat ggaaatactt    240
tatattccat ttgtttcatc atattcatat atcccttt                            278
```

<210> SEQ ID NO 8
<211> LENGTH: 73
<212> TYPE: DNA
<213> ORGANISM: Homo sapiens

<400> SEQUENCE: 8

| | | | | | | |
|---|---|---|---|---|---|---|
| cattggatac | tccatcacct | gctgtgatat | tatgaatgtc | tgcctatata | aatattcact | 60 |
| attccataac | aca | | | | | 73 |

<210> SEQ ID NO 9
<211> LENGTH: 3033
<212> TYPE: DNA
<213> ORGANISM: Homo sapiens

<400> SEQUENCE: 9

| | | | | | | |
|---|---|---|---|---|---|---|
| actaacataa | agctgaaggt | gaataaaaaa | atcagggtta | gccaaacaaa | ttttcatggt | 60 |
| caaataccac | ataaaagta | aatatactta | agttcccagc | aaaatctgaa | ttgaacgtag | 120 |
| acaaaatgct | catttctcag | tgtttgacag | acttaacagt | ttgagccaat | aaaaatgtac | 180 |
| tgactagata | aactactaaa | agttgttaat | ttttgcaatg | tatatttctg | aaaagaaagt | 240 |
| ttatctatta | tagaaattcc | tgtgcccatt | taagaacttt | gagcatttta | attgttaat | 300 |
| aatatagttt | aattgcatca | tgaaaataat | caataataca | atttatttgg | tttatttaaa | 360 |
| aaaactgatt | ctttctgctc | tctctatata | tagactgatt | ttatactaat | gttgcctaaa | 420 |
| gatcaccaaa | ttgtttgaag | cctaggtttc | tgagggatgg | aaaatgatgt | cacaactatt | 480 |
| tacagttcac | acacacattc | tgggattta | atacatcctt | tacaagtgca | ggaaaggtgg | 540 |
| aagattgatg | atttggggga | attagagcta | ccacacccca | gagggtggta | tggtatgttg | 600 |
| tctgttgtga | gctgtgtgaa | tcagagagtt | tgatttagac | atatatttag | aaagaggaaa | 660 |
| gatgaaccaa | tcaaaaataa | taactataat | gactttttcaa | gatatagaca | atacagttaa | 720 |
| gatataaatg | gaaacaaaaa | aagttaaaag | tggggagatg | aagtctgatt | ttttggtttt | 780 |
| tttttttttt | tgcttttttg | tttgtttatg | taatcagtgt | taccagttta | aaataatggg | 840 |
| ttataagaca | ctatatgcaa | gcctcatggt | aacctccaat | ctaaaacata | caacaaatac | 900 |
| acacaaaata | aaaaggagaa | attaaaacac | accaccagag | aaaatcacct | acattaaaag | 960 |
| aaagacaaat | aggaagaaaa | taagaaagag | aaggccatca | ataatcaga | aaatgaataa | 1020 |
| caaaatgaca | ggaataagtc | ctcataaata | ataacattga | atgtaaatgg | actaagctct | 1080 |
| ccaatgaaag | acagggagtg | gctgaatgta | ttttaaaaaa | aatattacac | cgagctgtgc | 1140 |
| gtggtgtctc | acacctataa | tcccagcatt | ttgggagact | gagccgggtg | gatcacttga | 1200 |
| gcccaggagt | tcgagaccag | cctggccaac | atggcaaaac | cctgtctcta | ctaaaaatac | 1260 |
| aaaaaattag | ctgaacatgg | tggcacatgc | ctgtggttcc | agctactaga | gaggctgagg | 1320 |
| cagaagaatt | gcttgaactt | gggaggtgga | ggttgcagtg | agctaagatt | gatggagcca | 1380 |
| ctgcacccca | gcctaggtga | cagaataaga | ctctgcctca | aaaaaaaaaa | gcaaacaaa | 1440 |
| acaaacaaa | aaacccttag | acccaatgat | tcattgccta | caagaagtat | gcttcacctt | 1500 |
| taaagacaca | tatagactga | aggtaaaggg | atggaaaaat | attctatgcc | tatgaaaca | 1560 |
| aacaaaaga | agcagaagct | acatttatat | cagacaaaat | agactgcaag | acaaaaacta | 1620 |
| tgaaaagaga | gaaagaaggt | cattatatag | tgataaaggg | gtccatttag | caagagcatt | 1680 |
| taacaattct | aaatatatat | tcacccaata | ctggagtact | caggtatata | aagcaaatat | 1740 |

-continued

```
tattagagcc aaagagagag atagacagac ccccatacaa taataactgg agacttcaac   1800
accccacttt cagcattgga cagatcatcc agacagaaaa ttaacaaaca tcaaatttca   1860
tctgcaccat aggtcaaatg gacctagtag atatttacag aacatttgat ccaacagctg   1920
tagaatacac attcttctcc tcagcacatg gataattctc aaggatatac caaatgctag   1980
gtcacaaaac aaatcttaaa atttagaaaa aaagtgaaat aatatcaaac gttttctctc   2040
accacagact aagaaaaaaa gaagtcccaa ataaatacaa tctgagataa aaaaggagac   2100
gagacaacca ataccacaaa aaattaaagg atcattagaa gatactatga aactatatgc   2160
taataaattg gaaaacctga acaaaataga taattcctag aaacatacaa catactggtc   2220
tgttcaggtt ttgtattttt tcatagtacc atgaagaaat acaagaattg tttctagaac   2280
cattcttgta tttcttcatg gttttttgtat ttcttcatgg aaccatgaag aaatacaaaa   2340
tgtgaacagg ccaataacaa gtaatgagac agaagccata ctaaaaagta tcccagaaaa   2400
gaactcagga tctgatggct tcactgatga attttgccaa atatttaaaa aactaatacc   2460
aatccaactc aaattattaa aaaaatagag gtggacagaa tctttccaaa tgtattctat   2520
gaggccagtg ttttttctga ttgaatctcc cattatattt taatcacata taaaaccaga   2580
gaaagacaca ttaaaaagaa agaaaactgt aggccaatat ctctgatgaa cattgatgca   2640
gaaatcctca acaacaaatt agcaaactga attcaagaac acattaaaac aatcattcat   2700
catgaccaag tggaatttgt cctagagatt caagtgtggt taggtatgtg cagatcaatg   2760
ggtttaatgt tgtccaatga acataatgtc ctccagctcc atccatgttc ttgcaaatga   2820
caggatctca ttctttttta tggctaagta gtactccatt gtgtataagt gccatatttt   2880
ctttatccat tcatctgtta gacacctaag ttgcttccaa atcttagcta ttgtgaatag   2940
tgctgcaata acatgggag tgtaaatatt ttgttgacat actgatttca tttcctttgg   3000
ataaataccc agtagtggga ttgctggatc ata                                3033
```

<210> SEQ ID NO 10
<211> LENGTH: 14
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 11
<223> OTHER INFORMATION: n =a, g, c or t

<400> SEQUENCE: 10
yyyyyyyyyy nyag                                                      14

METHODS OF IMPROVING HOMOLOGOUS RECOMBINATION

BACKGROUND OF THE INVENTION

Current approaches to treating disease by administering therapeutic proteins include in vitro production of therapeutic proteins for conventional pharmaceutical delivery (e.g. intravenous, subcutaneous, or intramuscular injection) and, more recently, gene therapy.

Proteins of therapeutic interest can be produced by introducing exogenous DNA encoding the protein of therapeutic interest into appropriate cells. For example, a vector which includes exogenous DNA encoding a therapeutic protein can be introduced into cells and the encoded protein expressed. It has also been suggested that endogenous cellular genes and their expression may be modified by gene targeting. See for example, U.S. Pat. Nos. 5,272,071, 5,641,670, WO 91/06666, WO 91/06667 and WO 90/11354.

SUMMARY OF THE INVENTION

The invention is based, in part, on the use of homologous recombination between a double stranded DNA sequence and a selected target DNA, e.g., chromosomal DNA in a cell, promoted by providing an agent which enhances homologous recombination, e.g., Rad52, and an agent which inhibits non-homologous end joining, e.g., a Ku inactivating agent, in sufficiently close proximity to the DNA sequence at the targeted site. It is predicted that a higher rate of homologous recombination occurred in the presence of both Rad52 and a Ku inactivating agent than in their absence. In addition, it is predicted that gene targeting aimed at altering a targeted site in a DNA, e.g., a targeted site in the chromosomal DNA in a cell, using a selected DNA sequence as a template can be promoted by providing a Rad52 protein and a Ku inactivating agent, e.g., an anti-Ku antibody. By providing a Rad52 protein and a Ku inactivating agent in close proximity to the selected DNA sequence and the target site, a higher rate of alteration by gene targeting occurs than in the absence of a Rad52 protein and a Ku inactivating agent, e.g., an anti-Ku antibody.

Accordingly, in one aspect, the invention features, a method of promoting an alteration at a selected site in a target DNA, e.g., in the chromosomal DNA of a cell. The method includes providing, at the site: (a) a double stranded DNA sequence which includes a selected DNA sequence; (b) an agent which enhances homologous recombination, e.g., a Rad52 protein or a functional fragment thereof, or a DNA sequence which encodes Rad52 or a functional fragment thereof; and (c) an agent which inhibits non-homologous end joining, e.g., an agent which inactivates Ku, and allowing the alteration to occur. In a preferred embodiment, components (a), (b), and (c) are provided, e.g., introduced into the cell, such that, at the site of an interaction between the selected DNA sequence and the target DNA, the concentration of the agent which enhances homologous recombination and of the agent which inhibits non-homologous end joining are sufficient that an alteration of the site, e.g., homologous recombination or gene correction between the selected DNA sequence and the target DNA, occurs at a higher rate than would occur in the absence of the supplied agent which enhances homologous recombination and the agent which inhibits non-homologous end joining. The agent which inhibits non-homologous end joining is preferably provided locally. Preferably the agent which inhibits non-homologous end joining is a Ku inactivating agent such as an anti-Ku antibody.

Components (a), (b), and (c) can be introduced together, which is preferred, or separately. In addition, two of the components can be introduced together and the third can be introduced separately. For example, the DNA sequence and the agent which enhances homologous recombination, e.g., Rad52, can be introduced together or the DNA sequence and the agent which inhibits non-homologous end joining, e.g., a Ku inactivating agent, can be introduced together. In another preferred embodiment, the agent which enhances homologous recombination and the agent which inhibits non-homologous end joining can be introduced together.

Two, or preferably all, of the components can be provided as a complex. In a preferred embodiment, the method includes contacting the target DNA, e.g., by introducing into the cell, a complex which includes: (a) a double stranded DNA sequence which includes the selected DNA sequence; (b) an agent which enhances homologous recombination, e.g., a Rad52 protein or functional fragment thereof; and (c) an agent which inhibits non-homologous end joining, e.g., a Ku inactivating agent such as an anti-Ku antibody or a Ku-binding oligomer or polymer.

In a preferred embodiment, one, or more, preferably all of the components are provided by local delivery, e.g., microinjection, and are not expressed from the target genome or another nucleic acid. In a particularly preferred embodiment, the agent which inhibits non-homologous end joining, e.g., a Ku inhibiting agent, is provided by local delivery, e.g., microinjection, and is not expressed from the target genome or another nucleic acid.

In a preferred embodiment, the agent which inhibits non-homologous end joining is: an agent which inactivates hMre11, e.g., an anti-hMre11 antibody or a hMre11-binding oligomer or polymer; an agent which inactivates hRad50, e.g., an anti-hRad50 antibody or a hRad50-binding oligomer or polymer; an agent which inactivates Nbs1, e.g., an anti-Nbs1 antibody or a hNbs1-binding oligomer or polymer; an agent which inactivates human ligase 4 (hLig4), e.g., an anti-hLig4 antibody or a hLig4-binding oligomer or polymer; an agent which inactivates hXrcc4, e.g., an anti-hXrcc4 antibody or a hXrcc4-binding oligomer or polymer; an agent which inactivates a human homolog of Rap1, e.g., an antibody to a human homolog of Rap1 or an oligomer or polymer which binds a human homolog of Rap1; an agent which inactivates a human homolog of Sir2304, e.g., an antibody to a human homolog of Sir2304 or an oligomer or polymer which binds a human homolog of Sir2304; an agent which inactivates Ku, e.g., an anti-Ku antibody or a Ku-binding oligomer or polymer. Any of the agents which inhibit non-homologous end joining can be administered alone or can be administered in combination with one or more of the other agents which inhibit non-homologous end joining.

In a preferred embodiment, the DNA sequence is a linear DNA sequence. In a preferred embodiment, the linear DNA sequence can have one or more single stranded overhang(s).

In a preferred embodiment, the selected DNA sequence is flanked by a targeting sequence. The targeting sequence is homologous to the target, e.g., homologous to DNA adjacent to the site where the target DNA is to be altered or to the site where the selected DNA sequence is to be integrated. Such flanking sequence can be present at one or more, preferably both ends of the selected DNA sequence. If two flanking sequences are present, one should be homologous with a first region of the target and the other should be homologous to a second region of the target.

In a preferred embodiment, the DNA sequence has one or more protruding single stranded end, e.g., one or both of the protruding ends are 3' ends or 5' ends.

In a preferred embodiment, the agent which enhances homologous recombination is: a Rad52 protein or a functional fragment thereof; a Rad51 protein or a functional fragment thereof; a Rad54 protein or a functional fragment thereof; or a combination thereof.

In a preferred embodiment, the agent which enhances homologous recombination is adhered to, e.g., coated on, the DNA sequence. In a preferred embodiment, the Rad52 protein or functional fragment thereof is adhered to, e.g., coated on, the DNA sequence.

In a preferred embodiment, the Rad52 protein or fragment thereof is human Rad52 (hRad52).

In a preferred embodiment, the anti-Ku antibody is: an anti-Ku70 antibody; an anti-Ku80 antibody. In a preferred embodiment, the anti-Ku antibody is: a humanized antibody; a human antibody; an antibody fragment, e.g., a Fab, Fab', $F(ab')^2$ or $F(v)$ fragment.

In a preferred embodiment, at least one anti-Ku antibody is covalently linked to: the DNA sequence; the Rad52 protein or fragment thereof. In another preferred embodiment, at least one anti-Ku antibody is non-covalently linked to: the DNA sequence; the Rad52 protein or fragment thereof.

In a preferred embodiment, an anti-Ku70 antibody and an anti-Ku80 antibody is provided, e.g., as components of a complex.

In a preferred embodiment, the cell is: a eukaryotic cell. In a preferred embodiment, the cell is of fungal, plant or animal origin, e.g., vertebrate origin. In a preferred embodiment, the cell is: a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; a transformed or immortalized cell line. Preferably, the cell is a human cell. Examples of immortalized human cell line useful in the present method include, but are not limited to: a Bowes Melanoma cell (ATCC Accession No. CRL 9607), a Daudi cell (ATCC Accession No. CCL 213), a HeLa cell and a derivative of a HeLa cell (ATCC Accession Nos. CCL2 CCL2.1, and CCL 2.2), a HL-60 cell (ATCC Accession No. CCL 240), a HT1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Rafji cell (ATCC Accession No. CCL 86), a RPMI 8226 cell (ATCC Accession No. CCL 155), a U-937 cell (ATCC Accession No. 1593), WI-28VA13 sub line 2R4 cells (ATCC Accession No. CLL 155), a CCRF-CEM cell (ATCC Accession No. CCL 119) and a 2780AD ovarian carcinoma cell (Van Der Blick et al., Cancer Res. 48:5927–5932, 1988), as well as heterohybridoma cells produced by fusion of human cells and cells of another species. In another embodiment, the immortalized cell line can be cell line other than a human cell line, e.g., a CHO cell line, a COS cell line.

In a preferred embodiment, the components, e.g., the components of a complex, are introduced into the cell by microinjection.

In one preferred embodiment, the selected DNA sequence differs from the target DNA by less than 10, 8, 6, 5, 4, 3, 2, or by a single nucleotide, e.g., by a substitution, or a deletion, or an insertion.

In a preferred embodiment, the target DNA includes a mutation, e.g., the target sequence differs from wild-type sequence by about 10, 8, 6, 5, 4, 3, 2 or by a single nucleotide. Preferably, the mutation is a point mutation, e.g., a mutation due to an insertion, deletion or a substitution.

In a preferred embodiment, the target DNA includes a mutation and the mutation is associated with, e.g., causes, contributes to, conditions or controls, a disease or a dysfunction. Preferably, the disease or dysfunction is: cystic fibrosis; sickle cell anemia; hemophilia A; hemophilia B; von Willebrand disease type 3; xeroderma pigmentosa; thalassaemias; Lesch-Nylan syndrome; protein C resistance; a lysosomal storage disease, e.g., Gaucher disease, Fabry disease; mucopolysaccharidosis (MPS) type 1 (Hurley-Scheie syndrome), MPS type II (Hunter syndrome), MPS type IIIA (Sanfilio A syndrome), MPS type IIIB (Sanfilio B syndrome), MPS type IIIC (Sanfilio C syndrome), MPS type IIID (Sanfilio D syndrome), MPS type IVA (Morquio A syndrome), MPS type IVB (Morquio B syndrome), MPS type VI (Maroteaux-Larry syndrome), MPS type VII (Sly syndrome).

In a preferred embodiment, the target DNA includes a mutation and the selected DNA sequence includes a normal wild-type sequence which can correct the mutation.

In a preferred embodiment, the target DNA includes a mutation and the mutation is in the cystic fibrosis transmembrane regulator (CFTR) gene. Preferably, the mutation is one which alters the amino acid at codon 508 of the CFTR protein coding region, e.g., the mutation is a 3 base pair in-frame deletion which eliminates a phenylalanine at codon 508 of the CFTR protein. This deletion of phenylalanine-508 in the CFTR protein is found in a high percentage of subjects having cystic fibrosis. Thus, in a preferred embodiment, a selected DNA sequence including sequence encoding phenylalanine-508 as found in the wild-type CFTR gene can be used to target and correct the mutated CFTR gene.

In a preferred embodiment, the target DNA includes a mutation and the mutation is in the human β-globin gene. Preferably, the mutation is one which alters the amino acid at the sixth codon of the β-globin gene, e.g., the mutation is an A to T substitution in the sixth codon of the β-globin gene. This mutation leads to a change from glutamic acid to valine in the β-globin protein which is found in subjects having sickle cell anemia. Thus, in a preferred embodiment, a selected DNA which encodes a wild-type amino acid residue at codon 6, e.g., a selected DNA sequence including an A as found within the sixth codon of wild-type β-globin gene, can be used to target and correct the mutated β-globin gene.

In a preferred embodiment, the target DNA includes a mutation and the mutation is in the Factor VIII gene. For example, a mutation can be in exon 23, 24, and/or exon 25 of the Factor VIII gene. Preferably, the mutation is one which alters the amino acid at codon 2209 of the coding region of the Factor VIII protein coding region, e.g., the mutation is a G to A substitution in exon 24 of the Factor VIII gene which leads to a change from an arginine to a glutamine at amino acid 2209 of Factor VIII. Preferably, the mutation is one which alters the amino acid at codon 2229 of the coding region of the Factor VIII protein coding region, e.g., the mutation is a G to T substitution in exon 25 of the Factor VIII gene which leads to a change from a tryptophan to a cysteine at amino acid 2229 of Factor VIII. These mutations have been associated with moderate to severe hemophilia A. Thus, in a preferred embodiment, a selected DNA sequence including either DNA which encodes a wild-type amino acid at codon 2209 of the coding region of Factor VIII gene or DNA which encodes a wild-type amino acid at codon 2229 of the coding region of the Factor VIII gene, or both, can be used to target and correct the mutated Factor VIII gene.

In a preferred embodiment, the target DNA includes a mutation and the mutation is in the Factor IX gene. For example, in subjects having hemophilia B, most of the mutations are point mutations in the Factor IX gene. Thus, in a preferred embodiment, the selected DNA sequence can include one or more nucleotides having at least one nucleotide from the wild-type Factor IX gene, to target and correct one or more of the point mutations in the Factor IX gene associated with hemophilia B.

In a preferred embodiment, the target DNA includes a mutation and the mutation is in the von Willebrand factor gene. Preferably, the mutation is a single cytosine deletion in a stretch of 6 cytosines at positions 2679–2684 in exon 18 of the von Willebrand gene. This mutation is found in a significant percentage of subjects having von Willebrand disease type 3. Other mutations, e.g., point mutations, associated with von Willebrand disease type 3 can also be altered as described herein. Thus, in a preferred embodiment, a selected DNA sequence including sequences found in the wild-type von Willebrand gene, e.g., the six cytosines at positions 2679–2684 of the von Willebrand gene, can be used to target and correct the mutated von Willebrand gene.

In a preferred embodiment, the target DNA includes a mutation and the mutation is in the Xeroderma pigmentosum group G (XP-G) gene. Preferably, the mutation is a deletion of a single adenine in a stretch of three adenines at positions 19–21 of a 245 base-pair exon found in the XP-G gene. This deletion leads to xeroderma pigmentosum. Thus, in a preferred embodiment, a selected DNA including the wild-type sequence of the XP-G gene, e.g., three adenines at positions 19–21 of the 245 base-pair exon, can be used to target and correct the mutated XP-G gene.

Preferably, an agent which inactivates a mismatch repair protein such as Msh2, Msh6, Msh3, Mlh1, Pms2, Mlh3, Pms1, is also provided. The agent can be included in a complex.

In another preferred embodiment, the alteration includes homologous recombination between the selected DNA sequence and the target DNA, e.g., a chromosome.

In preferred embodiment, the selected DNA sequence differs from the target DNA by more than one nucleotide, e.g., it differs from the target by a sufficient number of nucleotides such that the target, or the selected DNA sequence has an unpaired region, e.g., a loop-out region. In such an application, Msh2, Msh6, Msh3, Mlh1, Pms2, Mlh3, Pms1 can also be provided, e.g., as part of a complex.

In a preferred embodiment, the alteration includes integration of the selected sequence into the target DNA and the selected DNA is integrated such that it is in a preselected relationship with a preselected element on the target, e.g., if one is a regulatory element and the other is a sequence which encodes a protein, the regulatory element functions to regulate expression of the protein encoding sequence. Flanking sequences which promote the selected integration can be used. The selected DNA sequence can be integrated 5', 3', or within, a selected target sequence, e.g., a gene or coding sequence.

In a preferred embodiment, the alteration includes integration of the selected DNA sequence and the selected DNA sequence is a regulatory sequence, e.g., an exogenous regulatory sequence. In a preferred embodiment, the regulatory sequence includes one or more of: a promoter, an enhancer, an upstream activating sequence (UAS), a scaffold-attachment region or a transcription factor-binding site. In a preferred embodiment, the regulatory sequence includes: a regulatory sequence from a metallothionein-I gene, e.g., a mouse metallothionein-I gene, a regulatory sequence from an SV-40 gene, a regulatory sequence from a cytomegalovirus gene, a regulatory sequence from a collagen gene, a regulatory sequence from an actin gene, a regulatory sequence from an immunoglobulin gene, a regulatory sequence from the HMG-CoA reductase gene, a regulatory sequence from γ actin gene, a regulatory sequence from transcription activator YY1 gene, a regulatory sequence from fibronectin gene, or a regulatory sequence from the EF-1α gene.

In a preferred embodiment, the selected DNA sequence includes an exon. Preferably, the exogenous exon includes: a CAP site, the nucleotide sequence ATG, and/or encoding DNA in-frame with the targeted endogenous gene.

In a preferred embodiment, the selected DNA sequence includes a splice-donor site.

In a preferred embodiment, the selected DNA sequence includes an exogenous regulatory sequence which when integrated into the target functions to regulate an endogenous coding sequence. The selected DNA sequence can be integrated upstream of the coding region of an endogenous gene in the target or upstream of the endogenous regulatory sequence of an endogenous gene in the target. In another preferred embodiment, the selected DNA sequence can be integrated downstream of an endogenous gene or coding region or within an intron or an endogenous gene. In another preferred embodiment, the selected DNA sequence can be integrated such that the endogenous regulatory sequence of the endogenous gene is inactive, e.g., is wholly or partially deleted.

In a preferred embodiment, the selected DNA sequence is upstream of an endogenous gene and is linked to the second exon of the endogenous gene.

In a preferred embodiment, the endogenous gene encodes: a hormone, a cytokine, an antigen, an antibody, an enzyme, a clotting factor, a transport protein, a receptor, a regulatory protein, a structural protein or a transcription factor. In a preferred embodiment, the endogenous gene encodes any of the following proteins: erythropoietin, calcitonin, growth hormone, insulin, insulinotropin, insulin-like growth factors, parathyroid hormone, α2-interferon (IFNA2), β-interferon, γ-interferon, nerve growth factors, FSHβ, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-granulocyte (GCSF), CSF-macrophage, CSF-granulocyte/macrophage, immunoglobulins, catalytic antibodies, protein kinase C, glucocerebrosidase, superoxide dismutase, tissue plasminogen activator, urokinase, antithrombin III, DNAse, α-galactosidase, tyrosine hydroxylase, blood clotting factor V, blood clotting factor VII, blood clotting factor VIII, blood clotting factor IX, blood clotting factor X, blood clotting factor XIII, apolipoprotein E, apolipoprotein A-I, globins, low density lipoprotein receptor, IL-2 receptor, IL-2 antagonists, α-1-antitrypsin, immune response modifiers, β-glucoceramidase, α-iduronidase, α-L-iduronidase, glucosamine-N-sulfatase, α-N-acetylglucosaminidase, acetylcoenzymeA:α-glucosamine-N-acetyltransferase, N-acetylglucosamine-6-sulfatase, β-galactosidase, β-glucuronidase, N-acetylgalactosamine-6-sulfatase, and soluble CD4.

In a preferred embodiment, the endogenous gene encodes follicle stimulating hormone β(FSHβ) and the selected DNA sequence includes a regulatory sequence, e.g., a regulatory sequence which differs in sequence from the regulatory sequence of the FSHβ gene. Preferably, the selected DNA sequence is flanked by a targeting sequence, e.g., such targeting sequence is present at one or more, preferably both ends of the selected DNA sequence. In a preferred embodiment, the targeting sequence is homologous to a region 5' of the FSHβ coding region (SEQ ID NO:1). In a preferred embodiment, the targeting sequence directs homologous recombination within the FSHβ coding sequence or upstream of the FSHβ coding sequence. In a preferred embodiment, the targeting sequence includes at least 20, 30, 50, 100 or 1000 contiguous nucleotides from SEQ ID NO:2, which corresponds to nucleotides −7454 to −1417 of human FSHβ sequence (numbering is relative to the translation start site), or SEQ ID NO:3, which corresponds to nucleotides −696 to −155 of human FSHβ sequence.

In a preferred embodiment, the endogenous gene encodes interferon α2 (IFNα2) and the selected DNA sequence includes a regulatory sequence, e.g., a regulatory sequence which differs in sequence from the regulatory sequence of the IFNα2 gene. Preferably, the selected DNA sequence is flanked by a targeting sequence, e.g., such targeting sequence is present at one or more, preferably both ends of the selected DNA sequence. In a preferred embodiment, the targeting sequence is homologous to a region 5' of the IFNα2 coding region. In a preferred embodiment, the targeting sequence directs homologous recombination within a region upstream of the IFNα2 coding sequence. In a preferred embodiment, the targeting sequence includes at least 20, 30, 50, 100 or 1000 contiguous nucleotides from SEQ ID NO:4, which corresponds to nucleotides −4074 to −511 of human IFNα2 sequence (numbering is relative to the translation start site). For example, it can include: at least 20, 30, 50, or 100 nucleotides from SEQ ID NO:7, which corresponds to nucleotides −4074 to −3796 of human IFNα2 sequence; at least 20, 30, or 50 nucleotides from SEQ ID NO:8, which corresponds to nucleotides −582 to −510 of human IFNα2 sequence; at least 20, 30, 50, 100, or 1000 nucleotides from SEQ ID NO:9, which corresponds to nucleotides −3795 to −583 of human IFNα2 sequence.

In a preferred embodiment, the endogenous gene encodes granulocyte colony stimulating factor (GCSF) and the selected DNA sequence includes a regulatory sequence, e.g., a regulatory sequence which differs in sequence from the regulatory sequence of the GCSF gene. Preferably, the selected DNA sequence is flanked by a targeting sequence, e.g., such targeting sequence is present at one or more, preferably both ends of the selected DNA sequence. In a preferred embodiment, the targeting sequence is homologous to a region 5' of the GCSF coding region. In a preferred embodiment, the targeting sequence directs homologous recombination within the GCSF coding sequence or upstream of the GCSF coding sequence. In a preferred embodiment, the targeting sequence includes at least 20, 30, 50, 100 or 1000 contiguous nucleotides from SEQ ID NO:5, which corresponds to nucleotides −6,578 to 101 of human GCSF sequence (numbering is relative to the translation start site). For example, the target sequence can include 20, 30, 50, 100 or 1000 nucleotides from SEQ ID NO:6, which corresponds to nucleotides −6,578 to −364 of the human GCSF gene.

In another preferred embodiment, the DNA sequence includes a coding region, e.g., the selected DNA sequence encodes a protein. In a preferred embodiment, the coding region encodes: a hormone, a cytokine, an antigen, an antibody, an enzyme, a clotting factor, a transport protein, a receptor, a regulatory protein, a structural protein or a transcription factor. In a preferred embodiment, the coding region encodes any of the following proteins: erythropoietin, calcitonin, growth hormone, insulin, insulinotropin, insulin-like growth factors, parathyroid hormone, α2-interferon (IFNA2), β-interferon, γ-interferon, nerve growth factors, FSHβ, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-granulocyte (GCSF), CSF-macrophage, CSF-granulocyte/macrophage, immunoglobulins, catalytic antibodies, protein kinase C, glucocerebrosidase, superoxide dismutase, tissue plasminogen activator, urokinase, antithrombin III, DNAse, α-galactosidase, tyrosine hydroxylase, blood clotting factor V, blood clotting factor VII, blood clotting factor VIII, blood clotting factor IX, blood clotting factor X, blood clotting factor XIII, apolipoprotein E, apolipoprotein A-I, globins, low density lipoprotein receptor, IL-2 receptor, IL-2 antagonists, α-1-antitrypsin, immune response modifiers, β-glucoceramidase, α-iduronidase, α-L-iduronidase, glucosamine-N-sulfatase, α-N-acetylglucosaminidase, acetylcoenzymeA:α-glucosamine-N-acetyltransferase, N-acetylglucosamine-6-sulfatase, β-galactosidase, β-glucuronidase, N-acetylgalactosamine-6-sulfatase, and soluble CD4.

In a preferred embodiment, the selected DNA sequence can be integrated into the target such that it is under the control of an endogenous regulatory element. The selected DNA can be integrated downstream of an endogenous regulatory sequence or upstream of a coding region of an endogenous gene and downstream of the endogenous regulatory sequence of the gene. In another preferred embodiment, the selected DNA can be integrated downstream of an endogenous regulatory sequence such that the coding region of the endogenous gene is inactivated, e.g., is wholly or partially deleted.

In a preferred embodiment, the method further includes introducing an agent which inhibits a mismatch-repair protein, e.g., Msh2, Msh6, Msh3, Mlh1, Pms2, Mlh3, Pms1, or other mismatch repair proteins, or combinations thereof. Preferably, the agent is an agent which inhibits expression of a mismatch-repair protein, e.g., the agent is an antisense RNA. In a preferred embodiment, the agent is an antibody against a mismatch-repair protein. In a preferred embodiment, the antibody against the mismatch-repair protein is covalently or non-covalently linked to the complex.

In another aspect, the invention features, a composition, e.g., a complex of components, for promoting an alteration at a target DNA, e.g., a chromosome, e.g., a target DNA described herein, using a selected DNA sequence, e.g., a selected DNA sequence described herein, as a template. The composition includes: (a) a double stranded DNA sequence which includes a selected DNA sequence; (b) an agent which enhances homologous recombination, e.g., a Rad52 protein or a functional fragment thereof; and (c) an agent which inhibits non-homologous end joining, e.g., an agent which inactivates Ku. The composition can be used, for example, to alter the target DNA sequence by integration.

In a preferred embodiment, the agent which inhibits non-homologous end joining is: an agent which inactivates hMre11, e.g., an anti-hMre11 antibody or a hMre11-binding oligomer or polymer; an agent which inactivates hRad50, e.g., an anti-hRad50 antibody or a hRad50-binding oligomer or polymer; an agent which inactivates Nbs1, e.g., an anti-Nbs1 antibody or a hNbs1-binding oligomer or polymer; an agent which inactivates human ligase 4 (hLig4), e.g., an anti-hLig4 antibody or a hLig4-binding oligomer or polymer; an agent which inactivates hXrcc4, e.g., an anti-hXrcc4 antibody or a hXrcc4-binding oligomer or polymer; an agent which inactivates a human homolog of Rap1, e.g., an antibody to a human homolog of Rap1 or an oligomer or polymer which binds a human homolog of Rap1; an agent which inactivates a human homolog of Sir2304, e.g., an antibody to a human homolog of Sir2304 or an oligomer or polymer which binds a human homolog of Sir2304; an agent which inactivates Ku, e.g., an anti-Ku antibody or a Ku-binding oligomer or polymer. Any of the agents which inhibit non-homologous end joining can be administered alone or can be administered in combination with one or more of the other agents which inhibit non-homologous end joining.

In a preferred embodiment, the DNA sequence is a linear DNA sequence. In a preferred embodiment, the linear DNA sequence can have one or more single stranded overhang(s).

In a preferred embodiment, the selected DNA sequence is flanked by a targeting sequence. The targeting sequence is homologous to the target, e.g., homologous to DNA adjacent to the site where the target DNA is to be altered or to the site where the selected DNA sequence is to be integrated. Such flanking sequence can be present at one or more, preferably both ends of the selected DNA sequence. If two flanking sequences are present, one should be homologous to a first region of the target and the other should be homologous to a second region of the target.

In a preferred embodiment, the DNA sequence has one or more protruding single stranded end, e.g., one or both of the protruding ends are 3' ends or 5' ends.

In a preferred embodiment, the agent which enhances homologous recombination is: a Rad52 protein or a functional fragment thereof; a Rad51 protein or a functional fragment thereof; a Rad54 protein or a functional fragment thereof; or a combination thereof.

In a preferred embodiment, the agent which enhances homologous recombination is adhered to, e.g., coated on, the DNA sequence. In a preferred embodiment, the Rad52 protein or functional fragment thereof is adhered to, e.g., coated on, the selected DNA sequence.

In a preferred embodiment, the Rad52 protein or fragment thereof is human Rad52 (hRad52).

In a preferred embodiment, the anti-Ku antibody is: an anti-Ku70 antibody; an anti-Ku80 antibody. In a preferred embodiment, the anti-Ku antibody is: a humanized antibody; a human antibody; an antibody fragment, e.g., a Fab, Fab', $F(ab')_2$ or F(v) fragment.

In a preferred embodiment, at least one anti-Ku antibody is covalently linked to: the selected DNA sequence; the Rad52 protein or fragment thereof. In another preferred embodiment, at least one anti-Ku antibody is covalently linked to: the selected DNA sequence; the Rad52 protein or fragment thereof.

In a preferred embodiment, the composition includes an anti-Ku70 antibody and an anti-Ku80 antibody.

In a preferred embodiment, the selected DNA sequence differs from the target DNA by less than 10, 8, 6, 5, 4, 3, 2 or by a single nucleotide, e.g., a substitution, or a deletion, or an insertion.

In a preferred embodiment, the target DNA includes a mutation, e.g., the target sequence differs from wild-type sequence by about 10, 8, 6, 5, 4, 3, 2 or by a single nucleotide. Preferably, the mutation is a point mutation, e.g., a mutation due to an insertion, deletion or a substitution.

In a preferred embodiment, the target DNA includes a mutation and the mutation is associated with, e.g., causes, contributes to, conditions or controls, a disease or a dysfunction. Preferably, the disease or dysfunction is: cystic fibrosis; sickle cell anemia; hemophilia A; hemophilia B; von Willebrand disease type 3; xeroderma pigmentosa; thalassaemias; Lesch-Nylan syndrome; protein C resistance; a lysosomal storage disease, e.g., Gaucher disease, Fabry disease, mucopolysaccharidosis (MPS) type 1 (Hurley-Scheie syndrome), MPS type II (Hunter syndrome), MPS type IIIA (Sanfilio A syndrome), MPS type IIIB (Sanfilio B syndrome), MPS type IIIC (Sanfilio C syndrome), MPS type IIID (Sanfilio D syndrome), MPS type IVA (Morquio A syndrome), MPS type IVB (Morquio B syndrome), MPS type VI (Maroteaux-Larry syndrome), MPS type VII (Sly syndrome).

In a preferred embodiment, the target DNA includes a mutation and the selected DNA sequence includes a normal wild-type sequence which can correct the mutation.

In a preferred embodiment, the target DNA includes a mutation and the mutation is in the cystic fibrosis transmembrane regulator (CFTR) gene. Preferably, the mutation is one which alters the amino acid at codon 508 of the CFTR protein coding region, e.g., the mutation is a 3 base pair in-frame deletion which eliminates a phenylalanine at codon 508 of the CFTR protein. This deletion of phenylalanine-508 in the CFTR protein is found in a high percentage of subjects having cystic fibrosis. Thus, in a preferred embodiment, a selected DNA sequence including sequence encoding phenylalanine-508 as found in the wild-type CFTR gene can be used to target and correct the mutated CFTR gene.

In a preferred embodiment, the target DNA includes a mutation and the mutation is in the human β-globin gene. Preferably, the mutation is one which alters the amino acid at the sixth codon of the β-globin gene, e.g., the mutation is an A to T substitution in the sixth codon of the β-globin gene. This mutation leads to a change from glutamic acid to valine in the β-globin protein which is found in subjects having sickle cell anemia. Thus, in a preferred embodiment, a selected DNA which encodes a wild-type amino acid residue at codon 6, e.g., a selected DNA sequence including an A as found within the sixth codon of wild-type β-globin gene, can be used to target and correct the mutated β-globin gene.

In a preferred embodiment, the target DNA includes a mutation and the mutation is in the Factor VIII gene. For example, a mutation can be in exon 23, 24, and/or exon 25 of the Factor VIII gene. Preferably, the mutation is one which alters the amino acid at codon 2209 of the coding region of the Factor VIII protein coding region, e.g., the mutation is a G to A substitution in exon 24 of the Factor VIII gene which leads to a change from an arginine to a glutamine at amino acid 2209 of Factor VIII. Preferably, the mutation is one which alters the amino acid at codon 2229 of the coding region of the Factor VIII protein coding region, e.g., the mutation is a G to T substitution in exon 25 of the Factor VIII gene which leads to a change from a tryptophan to a cysteine at amino acid 2229 of Factor VIII. These mutations have been associated with moderate to severe hemophilia A. Thus, in a preferred embodiment, a selected DNA sequence including either DNA which encodes a wild-type amino acid at codon 2209 of the coding region of Factor VIII gene, or DNA which encodes a wild-type amino acid at codon 2229 of the coding region of the Factor VIII gene, or both, can be used to target and correct the mutated Factor VIII gene.

In a preferred embodiment, the target DNA includes a mutation and the mutation is in the Factor IX gene. For example, in subjects having hemophilia B, most of the mutations are point mutations in the Factor IX gene. Thus, in a preferred embodiment, the selected DNA sequence can include one or more nucleotides having at least one nucleotide from the wild-type Factor IX gene, to target and correct one or more of the point mutations in the Factor IX gene associated with hemophilia B.

In a preferred embodiment, the target DNA includes a mutation and the mutation is in the von Willebrand factor gene. Preferably, the mutation is a single cytosine deletion in a stretch of six cytosines at positions 2679–2684 in exon 18 of the von Willebrand gene. This mutation is found in a significant percentage of subjects having von Willebrand disease type 3. Other mutations, e.g., point mutations, associated with von Willebrand disease type 3 can also be altered as described herein. Thus, in a preferred embodiment, a selected DNA sequence including sequences found in the wild-type von Willebrand gene, e.g., the six cytosines at positions 2679–2684 in exon 18 of the von Willebrand gene, can be used to target and correct the mutated von Willebrand gene.

In a preferred embodiment, the target DNA includes a mutation and the mutation is in the Xeroderma pigmentosum group G (XP-G) gene. Preferably, the mutation is a deletion of a single adenine in a stretch of three adenines at positions 19–21 of a 245 base-pair exon found in the XP-G gene. This deletion leads to xeroderma pigmentosum. Thus, in a preferred embodiment, a selected DNA including the wild-type sequence of the XP-G gene, e.g., three adenines at positions 19–21 of the 245 base-pair exon of the XP-G gene, can be used to target and correct the mutated XP-G gene.

In another preferred embodiment, the selected DNA sequence differs from the target DNA by more than one nucleotide, e.g., it differs from the target by a sufficient number of nucleotides such that the target, or the selected DNA sequence has an unpaired region, e.g., a loop-out region. Preferably, an agent which inactivates a mismatch repair protein such as Msh2, Msh6, Msh3, Mlh1, Pms2, Mlh3, Pms1, or combinations thereof, is also included in the composition, e.g., the agent can be included in the complex.

In a preferred embodiment, the selected DNA sequence has a flanking sequence such that it can integrate in a preselected relationship with a preselected element on a target DNA. For example, if the selected DNA is a regulatory sequence and the target DNA encodes a protein, the flanking sequence is such that it will integrate the regulatory element so that it functions to regulate expression of the protein encoding sequence. Flanking sequences which promote the selected integration can be used. The selected DNA sequence can have a flanking sequence such that it can be integrated 5', 3' or within, a selected target sequence, e.g., a gene or coding region in the target.

In a preferred embodiment, the selected DNA sequence includes a regulatory sequence, e.g., an exogenous regulatory sequence. In a preferred embodiment, the regulatory sequence includes one or more of: a promoter, an enhancer, an UAS, a scaffold-attachment region or a transcription factor-binding site. In a preferred embodiment, the regulatory sequence includes: a regulatory sequence from a metallothionein-I gene, e.g., the mouse metallothionein-I gene, a regulatory sequence from an SV-40 gene, a regulatory sequence from a cytomegalovirus gene, a regulatory sequence from a collagen gene, a regulatory sequence from an actin gene, a regulatory sequence from an immunoglobulin gene, a regulatory sequence from the HMG-CoA reductase gene, a regulatory sequence from γ actin gene, a regulatory sequence from transcription activator YY1 gene, a regulatory sequence from fibronectin gene, or a regulatory sequence from the EF-1α gene.

In a preferred embodiment, the selected DNA sequence includes an exon. Preferably, the exogenous exon includes: a CAP site, the nucleotide sequence ATG, and/or encoding DNA in-frame with the targeted endogenous gene.

In a preferred embodiment, the selected DNA sequence includes a splice-donor site.

In a preferred embodiment, a composition which includes a selected DNA sequence having exogenous regulatory sequence can have a flanking sequence such that it is integrated into the target such that it functions to regulate expression of an endogenous sequence. The selected DNA can be integrated into the target upstream of the coding region of an endogenous gene or coding sequence in the target, or integrated into the target upstream of the endogenous regulatory sequence of an endogenous gene or coding sequence in the target. In another preferred embodiment, the selected DNA sequence can be integrated into the target such that the endogenous regulatory sequence of the endogenous gene is inactive, e.g., is wholly or partially deleted. The selected DNA sequence can be integrated into the target downstream of the endogenous gene or coding region, or integrated within an intron of an endogenous gene.

In a preferred embodiment, the selected DNA sequence includes a regulatory sequence, e.g., a regulatory sequence which differs in sequence from the regulatory sequence of the FSHβ gene. Preferably, the selected DNA sequence is flanked by a targeting sequence, e.g., such targeting sequence is present at one or more, preferably both ends of the selected DNA sequence. In a preferred embodiment, the targeting sequence is homologous to a region 5' of FSHβ coding region (SEQ ID NO:1). In a preferred embodiment, the targeting sequence directs homologous recombination within the FSHβ coding sequence, or upstream of the FSHβ coding sequence. In a preferred embodiment, the targeting sequence includes at least 20, 30, 50, 100 or 1000 contiguous nucleotides from SEQ ID NO:2, which corresponds to nucleotides –7454 to –1417 of human FSHβ sequence (numbering is relative to the translation start site), or SEQ ID NO:3, which corresponds to nucleotides –696 to –155 of human FSHβ sequence.

In a preferred embodiment, the selected DNA sequence includes a regulatory sequence, e.g., a regulatory sequence which differs in sequence from the regulatory sequence of the IFNα2 gene. Preferably, the selected DNA sequence is flanked by a targeting sequence, e.g., such targeting sequence is present at one or more, preferably both ends of the selected DNA sequence. In a preferred embodiment, the targeting sequence is homologous to a region 5' of IFNα2 coding region. In a preferred embodiment, the targeting sequence directs homologous recombination within a region upstream of the IFNα2 coding sequence. In a preferred embodiment, the targeting sequence includes at least 20, 30, 50, 100 or 1000 contiguous nucleotides from SEQ ID NO:4, which corresponds to nucleotides –4074 to –511 of human IFNα2 sequence (numbering is relative to the translation start site). For example, it can include: at least 20, 30, 50, or 100 nucleotides from SEQ ID NO:7, which corresponds to nucleotides –4074 to –3796 of human IFNα2 sequence; at least 20, 30, or 50 nucleotides from SEQ ID NO:8, which corresponds to nucleotides –582 to –510 of human IFNα2 sequence; at least 20, 30, 50, 100, or 1000 nucleotides from SEQ ID NO:9, which corresponds to nucleotides –3795 to –583 of human IFNα2 sequence.

In a preferred embodiment, the selected DNA sequence includes a regulatory sequence, e.g., a regulatory sequence which differs in sequence from the regulatory sequence of the GCSF gene. Preferably, the selected DNA sequence is flanked by a targeting sequence, e.g., such targeting sequence is present at one or more, preferably both ends of the selected DNA sequence. In a preferred embodiment, the targeting sequence is homologous to a region 5' of GCSF coding region. In a preferred embodiment, the targeting sequence directs homologous recombination: within the GCSF coding sequence; upstream of the GCSF coding sequence. In a preferred embodiment, the targeting sequence includes at least 20, 30, 50, 100 or 1000 contiguous nucleotides from SEQ ID NO:5, which corresponds to nucleotides −6,578 to 101 of human GCSF sequence (numbering is relative to the translation start site). For example, the target sequence can include 20, 30, 50, 100 or 1000 nucleotides from SEQ ID NO:6, which corresponds to nucleotides −6,578 to −364 of the human GCSF gene (numbering is relative to the translation start site).

In another preferred embodiment, the DNA sequence includes a coding region, e.g., the DNA sequence encodes a protein. In a preferred embodiment, the coding region encodes: a hormone, a cytokine, an antigen, an antibody, an enzyme, a clotting factor, a transport protein, a receptor, a regulatory protein, a structural protein or a transcription factor. In a preferred embodiment, the coding region encodes any of the following proteins: erythropoietin, calcitonin, growth hormone, insulin, insulinotropin, insulin-like growth factors, parathyroid hormone, α2-interferon (IFNA2), β-interferon, γ-interferon, nerve growth factors, FSHβ, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-granulocyte (GCSF), CSF-macrophage, CSF-granulocyte/macrophage, immunoglobulins, catalytic antibodies, protein kinase C, glucocerebrosidase, superoxide dismutase, tissue plasminogen activator, urokinase, antithrombin III, DNAse, α-galactosidase, tyrosine hydroxylase, blood clotting factor V, blood clotting factor VII, blood clotting factor VIII, blood clotting factor IX, blood clotting factor X, blood clotting factor XIII, apolipoprotein E, apolipoprotein A-I, globins, low density lipoprotein receptor, IL-2 receptor, IL-2 antagonists, α1-antitrypsin, immune response modifiers, β-glucoceramidase, α-iduronidase, α-L-iduronidase, glucosamine-N-sulfatase, α-N-acetylglucosaminidase, acetylcoenzymeA:α-glucosamine-N-acetyltransferase, N-acetylglucosamine-6-sulfatase, β-galactosidase, β-glucuronidase, N-acetylgalactosamine-6-sulfatase, and soluble CD4.

In a preferred embodiment, the selected DNA sequence can have a flanking sequence such that when it is integrated into the target it is under the control of an endogenous regulatory element. The selected DNA can be integrated downstream of an endogenous regulatory sequence or upstream of a coding region of an endogenous gene and downstream of the endogenous regulatory sequence of the gene. In another preferred embodiment, the selected DNA can be integrated downstream of an endogenous regulatory sequence such that the coding region of the endogenous gene is inactive, e.g., is wholly or partially deleted.

In a preferred embodiment, the composition, e.g., the complex, is introduced into a cell. Preferably, the cell is a eukaryotic cell. In a preferred embodiment, the cell is of fungal, plant or animal origin, e.g., vertebrate origin. In a preferred embodiment, the cell is: a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; a transformed or immortalized cell line. Preferably, the cell is a human cell. Examples of immortalized human cell line useful in the present method include, but are not limited to: a Bowes Melanoma cell (ATCC Accession No. CRL 9607), a Daudi cell (ATCC Accession No. CCL 213), a HeLa cell and a derivative of a HeLa cell (ATCC Accession Nos. CCL2 CCL2.1, and CCL 2.2), a HL-60 cell (ATCC Accession No. CCL 240), a HT1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Rafji cell (ATCC Accession No. CCL 86), a RPMI 8226 cell (ATCC Accession No. CCL 155), a U-937 cell (ATCC Accession No. 1593), WI-28VA13 sub line 2R4 cells (ATCC Accession No. CLL 155), a CCRF-CEM cell (ATCC Accession No. CCL 119) and a 2780AD ovarian carcinoma cell (Van Der Blick et al., Cancer Res. 48:5927–5932, 1988), as well as heterohybridoma cells produced by fusion of human cells and cells of another species. In another embodiment, the immortalized cell line can be cell line other than a human cell line, e.g., a CHO cell line, a COS cell line.

In a preferred embodiment, the composition further includes an agent which inhibits a mismatch-repair protein, e.g., Msh2, Msh6, Msh3, Mlh1, Pms2, Mlh3, Pms1, or other mismatch repair proteins, or combinations thereof. Preferably, the agent is an agent which inhibits expression of a mismatch-repair protein, e.g., the agent is an antisense RNA. In a preferred embodiment, the agent is an antibody against a mismatch-repair protein. In a preferred embodiment, the antibody against the mismatch-repair protein is covalently or non-covalently linked to one or more components of the composition.

In another aspect, the invention features, a method of providing a protein. The method includes: providing a cell made by a method described herein, and allowing the cell to express the protein.

In a preferred embodiment: the method includes: providing a cell in which the following components have been introduced at a targeted site for alteration: (a) a double stranded DNA sequence which includes a selected DNA sequence; (b) an agent which enhances homologous recombination, e.g., a Rad52 protein or a functional fragment thereof; and (c) an agent which inhibits non-homologous end joining, e.g., a Ku inactivating agent; and allowing the cell to express the protein. Expression of the protein can occur, for example, by allowing expression of a protein encoded by the DNA, or by activating expression of the protein.

In a preferred embodiment, components (a), (b), and (c) are provided, e.g., introduced into the cell, such that, at the site of an interaction between the selected DNA sequence and the target DNA, the concentrations of the agent which enhances homologous recombination and of the agent which inhibits non-homologous end joining are sufficient that an alteration of the site, e.g., homologous recombination or gene correction, between the selected DNA sequence and the target DNA, occurs at a higher rate than would occur in the absence of the supplied agent which enhances homologous recombination and the agent which inhibits non-homologous end joining. The agent which inhibits non-homologous end joining is preferably provided locally.

In a preferred embodiment, components (a), (b), and (c) can be introduced together or separately. In addition, two of the components can be introduced together and the third can be introduced separately. For example, the DNA sequence and the agent which enhances homologous recombination, e.g., Rad52, can be introduced together or the DNA sequence and the agent which inhibits non-homologous end joining, e.g., a Ku inactivating agent, can be introduced together. In another preferred embodiment, the agent which enhances homologous recombination and the agent which inhibits non-homologous end joining can be introduced together.

Two, or preferably all, of the components can be provided as a complex. In a preferred embodiment, the method includes contacting the target DNA, e.g., by introducing into the cell, a complex which includes: (a) a double stranded DNA sequence which includes the selected DNA sequence; (b) an agent which enhances homologous recombination, e.g., a Rad52 protein or functional fragment thereof; and (c) an agent which inhibits non-homologous end joining, e.g., an agent which inactivates Ku.

In a preferred embodiment, one, or more, preferably all of the components, are provided by local delivery, e.g., microinjection, and are not expressed from the target genome or other nucleic acid. In a particularly preferred embodiment, the agent which inhibits non-homologous end joining, e.g., a Ku-inactivating agent such as an anti-Ku antibody, is provided by local delivery, e.g., microinjection, and is not expressed from the target genome or other nucleic acid.

In a preferred embodiment, the agent which inhibits non-homologous end joining is: an agent which inactivates hMre11, e.g., an anti-hMre11 antibody or a hMre11-binding oligomer or polymer; an agent which inactivates hRad50, e.g., an anti-hRad50 antibody or a hRad50-binding oligomer or polymer; an agent which inactivates Nbs1, e.g., an anti-Nbs1 antibody or a hNbs1-binding oligomer or polymer; an agent which inactivates human ligase 4 (hLig4), e.g., an anti-hLig4 antibody or a hLig4-binding oligomer or polymer; an agent which inactivates hXrcc4, e.g., an anti-hXrcc4 antibody or a hXrcc4-binding oligomer or polymer; an agent which inactivates a human homolog of Rap1, e.g., an antibody to a human homolog of Rap1 or an oligomer or polymer which binds a human homolog of Rap1; an agent which inactivates a human homolog of Sir2304, e.g., an antibody to a human homolog of Sir2304 or an oligomer or polymer which binds a human homolog of Sir2304; an agent which inactivates Ku, e.g., an anti-Ku antibody or a Ku-binding oligomer or polymer. Any of the agents which inhibit non-homologous end joining can be administered alone or can be administered in combination with one or more of the other agents which inhibit non-homologous end joining.

In a preferred embodiment, the DNA sequence is a linear DNA sequence. In a preferred embodiment, the linear DNA sequence can have one or more single stranded overhang(s).

In a preferred embodiment, the selected DNA sequence is flanked by a targeting sequence. The targeting sequence is homologous to the target, e.g., homologous to DNA adjacent to the site where the target DNA is to be altered or to the site where the selected DNA sequence is to be integrated. Such flanking sequence can be present at one or more, preferably both ends of the selected DNA sequence. If two flanking sequences are present one should be homologous with a first region of the target and the other should be homologous to a second region of the target.

In a preferred embodiment, the DNA sequence has one or more protruding single stranded end, e.g., one or both of the protruding ends are 3' ends or 5' ends.

In a preferred embodiment, the agent which enhances homologous recombination is: a Rad52 protein or a functional fragment thereof; a Rad51 protein or a functional fragment thereof; a Rad54 protein or a functional fragment thereof; or a combination thereof.

In a preferred embodiment, the agent which enhances homologous recombination is adhered to, e.g., coated on, the DNA sequence. In a preferred embodiment, the Rad52 protein or functional fragment thereof is adhered to, e.g., coated, on the selected DNA sequence.

In a preferred embodiment, the Rad52 protein or fragment thereof is human Rad52 (hRad52).

In a preferred embodiment, the anti-Ku antibody is: an anti-Ku70 antibody; an anti-Ku80 antibody. In a preferred embodiment, the anti-Ku antibody is: a humanized antibody; a human antibody; an antibody fragment, e.g., a Fab, Fab', $F(ab')^2$ or $F(v)$ fragment.

In a preferred embodiment, at least one anti-Ku antibody is covalently linked to: the selected DNA sequence; the agent which enhances homologous recombination, e.g., the Rad52 protein or fragment thereof. In another preferred embodiment, at least one anti-Ku antibody is non-covalently linked to: the selected DNA sequence; the agent which enhances homologous recombination, e.g., the rad52 protein or fragment thereof.

In a preferred embodiment, the complex includes an anti-Ku70 antibody and an anti-Ku80 antibody provided, e.g., as components of a complex.

In a preferred embodiment, the cell is: a eukaryotic cell. In a preferred embodiment, the cell is of fungal, plant or animal origin, e.g., vertebrate origin. In a preferred embodiment, the cell is: a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; a transformed or immortalized cell line. Preferably, the cell is a human cell. Examples of immortalized human cell line useful in the present method include, but are not limited to: a Bowes Melanoma cell (ATCC Accession No. CRL 9607), a Daudi cell (ATCC Accession No. CCL 213), a HeLa cell and a derivative of a HeLa cell (ATCC Accession Nos. CCL2 CCL2.1, and CCL 2.2), a HL-60 cell (ATCC Accession No. CCL 240), a HT1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Rafji cell (ATCC Accession No. CCL 86), a RPMI 8226 cell (ATCC Accession No. CCL 155), a U-937 cell (ATCC Accession No. 1593), WI-28VA13 sub line 2R4 cells (ATCC Accession No. CLL 155), a CCRF-CEM cell (ATCC Accession No. CCL 119) and a 2780AD ovarian carcinoma cell (Van Der Blick et al., Cancer Res. 48:5927–5932, 1988), as well as heterohybridoma cells produced by fusion of human cells and cells of another species. In another embodiment, the immortalized cell line can be cell line other than a human cell line, e.g., a CHO cell line, a COS cell line.

In a preferred embodiment, the components, e.g., the components of a complex, are introduced into the cell by microinjection.

In a preferred embodiment, the method further includes introducing an agent which inhibits a mismatch-repair protein, e.g., Msh2, Msh6, Msh3, Mlh1, Pms2, Mlh3, Pms1, or other mismatch repair proteins or combinations thereof. Preferably, the agent is an agent which inhibits expression of a mismatch-repair protein, e.g., the agent is an antisense RNA. In a preferred embodiment, the agent is an antibody against a mismatch-repair protein. In a preferred embodiment, the antibody against the mismatch-repair protein is covalently or non-covalently linked to the complex.

In a preferred embodiment, the protein is expressed in vitro. In other preferred embodiments, the cell is provided in a subject, e.g., a human, and the protein is expressed in the subject. In a preferred embodiment, the protein is expressed in a subject and the cell is autologous, allogeneic or xenogeneic. Selected DNA can be introduced into a cell in vivo, or the cell can be removed from the subject, the selected DNA introduced ex vivo, and the cell returned to the subject.

In a preferred embodiment, the selected DNA sequence differs from the target DNA by less than 10, 8, 6, 5, 4, 3, 2, or by a single nucleotide, e.g., a substitution, or a deletion, or an insertion.

In a preferred embodiment, the target DNA includes a mutation, e.g., the target sequence differs from wild-type sequence by about 10, 8, 6, 5, 4, 3, 2 or by a single nucleotide. Preferably, the mutation is a point mutation, e.g., a mutation due to an insertion, deletion or a substitution.

In a preferred embodiment, the target DNA includes a mutation and the mutation is associated with, e.g., causes, contributes to, conditions or controls, a disease or a dysfunction. Preferably, the disease or dysfunction is: cystic fibrosis; sickle cell anemia; hemophilia A; hemophilia B; von Willebrand disease type 3; xeroderma pigmentosa; thalassaemias; Lesch-Nylan syndrome; protein C resistance; a lysosomal disease, e.g., Gaucher disease, Fabry disease, mucopolysaccharidosis (MPS) type 1 (Hurley-Scheie syndrome), MPS type II (Hunter syndrome), MPS type IIIA (Sanfilio A syndrome), MPS type IIIB (Sanfilio B syndrome), MPS type IIIC (Sanfilio C syndrome), MPS type IIID (Sanfilio D syndrome), MPS type IVA (Morquio A syndrome), MPS type IVB (Morquio B syndrome), MPS type VI (Maroteaux-Larry syndrome), MPS type VII (Sly syndrome).

In a preferred embodiment, the target DNA includes a mutation and the selected DNA sequence includes a normal wild-type sequence which can correct the mutation.

In a preferred embodiment, the target DNA includes a mutation and the mutation is in the cystic fibrosis transmembrane regulator (CFTR) gene. Preferably, the mutation is one which alters the amino acid at codon 508 of the CFTR protein-coding region, e.g., the mutation is a 3 base pair in-frame deletion which eliminates a phenylalanine at codon 508 of the CFTR protein. This deletion of phenylalanine-508 in the CFTR protein is found in a high percentage of subjects having cystic fibrosis. Thus, in a preferred embodiment, a selected DNA sequence including sequence encoding phenylalanine-508 as found in the wild-type CFTR gene can be used to target and correct the mutated CFTR gene.

In a preferred embodiment, the target DNA includes a mutation and the mutation is in the human β-globin gene. Preferably, the mutation is one which alters the amino acid at the sixth codon of the β-globin gene, e.g., the mutation is an A to T substitution in the sixth codon of the β-globin gene. This mutation leads to a change from glutamic acid to valine in the β-globin protein which is found in subjects having sickle cell anemia. Thus, in a preferred embodiment, a selected DNA which encodes a wild-type amino acid residue at codon 6, e.g., a selected DNA sequence including an A as found within the sixth codon of wild-type β-globin gene, can be used to target and correct the mutated β-globin gene.

In a preferred embodiment, the target DNA includes a mutation and the mutation is in the Factor VIII gene. For example, a mutation can be in exon 23, 24, and/or exon 25 of the Factor VIII gene. Preferably, the mutation is one which alters the amino acid at codon 2209 of the coding region of the Factor VIII protein coding region, e.g., the mutation is a G to A substitution in exon 24 of the Factor VIII gene which leads to a change from an arginine to a glutamine at amino acid 2209 of Factor VIII. Preferably, the mutation is one which alters the amino acid at codon 2229 of the coding region of the Factor VIII protein coding region, e.g., the mutation is a G to T substitution in exon 25 of the Factor VIII gene which leads to a change from a tryptophan to a cysteine at amino acid 2229 of Factor VIII. These mutations have been associated with moderate to severe hemophilia A. Thus, in a preferred embodiment, a selected DNA sequence including either DNA which encodes a wild-type amino acid at codon 2209 of the coding region of Factor VIII gene, or DNA which encodes a wild-type amino acid at codon 2229 of the coding region of the Factor VIII gene, or both, can be used to target and correct the mutated Factor VIII gene.

In a preferred embodiment, the target DNA includes a mutation and the mutation is in the Factor IX gene. For example, in subjects having hemophilia B, most of the mutations are point mutations in the Factor IX gene. Thus, in a preferred embodiment, the selected DNA sequence can include one or more nucleotides having at least one nucleotide from the wild-type Factor IX gene, to target and correct one or more of the point mutations in the Factor IX gene associated with hemophilia B.

In a preferred embodiment, the target DNA includes a mutation and the mutation is in the von Willebrand factor gene. Preferably, the mutation is a single cytosine deletion in a stretch of six cytosines at positions 2679–2684 in exon 18 of the von Willebrand gene. This mutation is found in a significant percentage of subjects having von Willebrand disease type 3. Other mutations, e.g., point mutations, associated with von Willebrand disease type 3 can also be altered as described herein. Thus, in a preferred embodiment, a selected DNA sequence including sequences found in the wild-type von Willebrand gene, e.g., the six cytosines at positions 2679–2684 in exon 18 of the von Willebrand gene, can be used to target and correct the mutated von Willebrand gene.

In a preferred embodiment, the target DNA includes a mutation and the mutation is in the Xeroderma pigmentosum group G (XP-G) gene. Preferably, the mutation is a deletion of a single adenine in a stretch of adenines at positions 19–21 of a 245 base-pair exon found in the XP-G gene. This deletion leads to xeroderma pigmentosum. Thus, in a preferred embodiment, a selected DNA including the wild-type sequence of XP-G gene, e.g., three adenines at positions 19–21 at the 245 base-pair exon of the XP-G gene, can be used to target and correct the mutated XP-G gene.

In another preferred embodiment, the alteration includes homologous recombination between the selected DNA sequence and the target DNA, e.g., a chromosome.

In preferred embodiment, the selected DNA sequence differs from the target DNA by more than one nucleotide, e.g., it differs from the target by a sufficient number of nucleotides such that the target, or the selected DNA sequence has an unpaired region, e.g., a loop-out region. In such an application, Msh2, Msh6, Msh3, Mlh1, Pms2, Mlh3, Pms1, or combinations thereof, can also be provided, e.g., as part of a complex.

In a preferred embodiment, the alteration includes integration of the selected sequence into the target DNA and the selected DNA is integrated such that it is in a preselected relationship with a preselected element on the target, e.g., if one is a regulatory element and the other is a sequence which encodes a protein, the regulatory element functions to control expression of the protein encoding sequence. Flanking sequences which promote the selected integration can be used. The selected DNA sequence can be integrated 5', 3', or within, a selected target sequence, e.g., a gene or coding sequence.

In a preferred embodiment, the alteration includes integration of the selected DNA sequence and the selected DNA sequence is a regulatory sequence, e.g., an exogenous regulatory sequence. In a preferred embodiment, the regulatory sequence includes one or more of: a promoter, an enhancer, an UAS, a scaffold-attachment region or a transcription factor-binding site. In a preferred embodiment, the regulatory sequence includes: a regulatory sequence from metallothionein-I gene, e.g., the mouse metallothionein gene, a regulatory sequence from an SV-40 gene, a regulatory sequence from a cytomegalovirus gene, a regulatory sequence from a collagen gene, a regulatory sequence from an actin gene, a regulatory sequence from an immunoglobulin gene, a regulatory sequence from the HMG-CoA reductase gene, a regulatory sequence from γ actin gene, a regulatory sequence from transcription activator YY1 gene, a regulatory sequence from fibronectin gene, or a regulatory sequence from the EF-1α gene.

In a preferred embodiment, the selected DNA sequence includes an exon. Preferably, the exogenous exon includes: a CAP site, the nucleotide sequence ATG, and/or encoding DNA in-frame with the targeted endogenous gene.

In a preferred embodiment, the selected DNA sequence includes a splice-donor site.

In a preferred embodiment, the selected DNA sequence includes an exogenous regulatory sequence which when integrated into the target functions to regulate expression of an endogenous gene. The selected DNA can be integrated upstream of the coding region of an endogenous gene in the target or upstream of the endogenous regulatory sequence of an endogenous gene or coding region in the target. In another preferred embodiment, the selected DNA can be integrated downstream of an endogenous gene or coding region or within an intron or endogenous gene. In another preferred embodiment, the endogenous regulatory sequence of the endogenous gene is inactive, e.g., is wholly or partially deleted.

In a preferred embodiment, the selected DNA sequence is upstream of the endogenous gene and is linked to the second exon of the endogenous gene.

In a preferred embodiment, the endogenous gene encodes: a hormone, a cytokine, an antigen, an antibody, an enzyme, a clotting factor, a transport protein, a receptor, a regulatory protein, a structural protein or a transcription factor. In a preferred embodiment, the endogenous gene encodes any of the following proteins: erythropoietin, calcitonin, growth hormone, insulin, insulinotropin, insulin-like growth factors, parathyroid hormone, β2-interferon (IFNA2), β-interferon, γ-interferon, nerve growth factors, FSHβ, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-granulocyte (GCSF), CSF-macrophage, CSF-granulocyte/macrophage, immunoglobulins, catalytic antibodies, protein kinase C, glucocerebrosidase, superoxide dismutase, tissue plasminogen activator, urokinase, antithrombin III, DNAse, α-galactosidase, tyrosine hydroxylase, blood clotting factor V, blood clotting factor VII, blood clotting factor VIII, blood clotting factor IX, blood clotting factor X, blood clotting factor XIII, apolipoprotein E, apolipoprotein A-I, globins, low density lipoprotein receptor, IL-2 receptor, IL-2 antagonists, α-I-antitrypsin, immune response modifiers, β-glucoceramidase, α-iduronidase, α-L-iduronidase, glucosamine-N-sulfatase, α-N-acetylglucosaminidase, acetylcoenzymeA:α-glucosamine-N-acetyltransferase, N-acetylglucosamine-6-sulfatase, β-galactosidase, β-glucuronidase, N-acetylgalactosamine-6-sulfatase, and soluble CD4.

In a preferred embodiment, the endogenous gene encodes follicle stimulating hormone β(FSHβ) and the selected DNA sequence includes a regulatory sequence, e.g., a regulatory sequence which differs in sequence from the regulatory sequence of the FSHβ gene. Preferably, the selected DNA sequence is flanked by a targeting sequence, e.g., such targeting sequence is present at one or more, preferably both ends of the selected DNA sequence. In a preferred embodiment, the targeting sequence is homologous to a region 5' of FSHβ coding region (SEQ ID NO:1). In a preferred embodiment, the targeting sequence directs homologous recombination within the FSHβ coding sequence or upstream of the FSHβ, coding sequence. In a preferred embodiment, the targeting sequence includes at least 20, 30, 50, 100 or 1000 contiguous nucleotides from SEQ ID NO:2, which corresponds to nucleotides −7454 to −1417 of human FSHβ sequence (numbering is relative to the translation start site), or SEQ ID NO:3, which corresponds to nucleotides −696 to −155 of human FSHβ sequence.

In a preferred embodiment, the endogenous gene encodes interferon α2 (IFNα2) and the selected DNA sequence includes a regulatory sequence, e.g., a regulatory sequence which differs in sequence from the regulatory sequence of the IFNα2 gene. Preferably, the selected DNA sequence is flanked by a targeting sequence, e.g., such targeting sequence is present at one or more, preferably both ends of the selected DNA sequence. In a preferred embodiment, the targeting sequence is homologous to a region 5' of IFNα2 coding region. In a preferred embodiment, the targeting sequence directs homologous recombination within a region upstream of the IFNα2 coding sequence. In a preferred embodiment, the targeting sequence includes at least 20, 30, 50, 100 or 1000 contiguous nucleotides from SEQ ID NO:4, which corresponds to nucleotides −4074 to −511 of human IFNα2 sequence (numbering is relative to the translation start site). For example, it can include: at least 20, 30, 50, or 100 nucleotides from SEQ ID NO:7, which corresponds to nucleotides −4074 to −3796 of human IFNα2 sequence; at least 20, 30, or 50 nucleotides from SEQ ID NO:8, which corresponds to nucleotides −582 to −510 of human IFNα2 sequence; at least 20, 30, 50, 100, or 1000 nucleotides from SEQ ID NO:9, which corresponds to nucleotides −3795 to −583 of human IFNα2 sequence.

In a preferred embodiment, the endogenous gene encodes granulocyte colony stimulating factor (GCSF) and the selected DNA sequence includes a regulatory sequence, e.g., a regulatory sequence which differs in sequence from the regulatory sequence of the GCSF gene. Preferably, the selected DNA sequence is flanked by a targeting sequence, e.g., such targeting sequence is present at one or more, preferably both ends of the selected DNA sequence. In a preferred embodiment, the targeting sequence is homologous to a region 5' of GCSF coding region. In a preferred embodiment, the targeting sequence directs homologous recombination within the GCSF coding sequence or upstream of the GCSF coding sequence. In a preferred embodiment, the targeting sequence includes at least 20, 30, 50, 100 or 1000 contiguous nucleotides from SEQ ID NO:5, which corresponds to nucleotides −6,578 to 101 of human GCSF sequence (numbering is relative to the translation start site). For example, the target sequence can include 20, 30, 50, 100 or 1000 nucleotides from SEQ ID NO:6, which corresponds to nucleotides −6,578 to −364 of the human GCSF gene (numbering is relative to the translation start site).

In another preferred embodiment, the DNA sequence includes a coding region, e.g., the DNA sequence encodes a protein. In a preferred embodiment, the coding region encodes: a hormone, a cytokine, an antigen, an antibody, an enzyme, a clotting factor, a transport protein, a receptor, a regulatory protein, a structural protein or a transcription factor. In a preferred embodiment, the coding region encodes any of the following proteins: erythropoietin, calcitonin, growth hormone, insulin, insulinotropin, insulin-like growth factors, parathyroid hormone, β-interferon, γ-interferon, nerve growth factors, FSHβ, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-granulocyte, CSF-macrophage, CSF-granulocyte/macrophage, immunoglobulins, catalytic antibodies, protein kinase C, glucocerebrosidase, superoxide dismutase, tissue plasminogen activator, urokinase, antithrombin III, DNAse, α-galactosidase, tyrosine hydroxylase, blood clotting factor V, blood clotting factor VII, blood clotting factor VIII, blood clotting factor IX, blood clotting factor X, blood clotting factor XIII, apolipoprotein E, apolipoprotein A-I, globins, low density lipoprotein receptor, IL-2 receptor, IL-2 antagonists, α-1-antitrypsin, immune response modifiers, β-glucoceramidase, α-iduronidase, α-L-iduronidase, glucosamine-N-sulfatase, α-N-acetylglucosaminidase, acetylcoenzymeA:α-glucosamine-N-acetyltransferase, N-acetylglucosamine-6-sulfatase, β-galactosidase, β-glucuronidase, N-acetylgalactosamine-6-sulfatase, and soluble CD4.

In a preferred embodiment, the selected DNA sequence can be integrated into the target downstream of an endogenous regulatory sequence or upstream of a coding region of an endogenous gene and downstream of the endogenous regulatory sequence of the gene. In another preferred embodiment, the selected DNA sequence can be integrated downstream of an endogenous regulatory sequence such that the coding region of the endogenous gene is inactive, e.g., is deleted.

In another aspect, the invention features, a cell made by any of the methods described herein.

In another aspect, the invention features a method of altering expression of a protein coding sequence of a gene in a cell, by any of the methods described herein.

In a preferred embodiment, the method includes introducing a complex described herein having a DNA sequence which includes a regulatory sequence into the cell; maintaining the cell under conditions which permit alteration of a targeted genomic sequence to produce a homologously recombinant cell; and maintaining the homologously recombinant cell under conditions which permit expression of the protein coding sequence of the gene under control of the regulatory sequence.

Maintaining the homologously recombinant cell under conditions which permit expression of the protein coding sequence of the gene under control of the regulatory sequence, thereby altering expression of the protein coding sequence of the gene.

The term "homologous" as used herein, refers to a targeting sequence that is identical to or sufficiently similar to a target site, e.g., a chromosomal DNA target site, so that the targeting sequence and the target site can undergo homologous recombination. A small percentage of base pair mismatches is acceptable, as long as homologous recombination can occur at a useful frequency.

As used herein, the term "wild-type" refers to a sequence which is not associated with, e.g., causes, contributes to, conditions or controls, a disease or dysfunction.

As used herein, a "complex" refers to a stable association in which the components are coupled by covalent or non-covalent bonds.

Other features and advantages of the invention will be apparent from the following detailed description, and from the claims.

DETAILED DESCRIPTION OF THE INVENTION

Agents which Enhance Homologous Recombination

Agents which enhance homologous recombination can be provided with a selected DNA sequence in order to promote homologous recombination between the selected DNA sequence and the target DNA, e.g., chromosomal DNA. Agents which enhance homologous recombination have one or more of the following functions: 1) increase homologous recognition between the selected DNA sequence and the selected site for integration; 2) increase homologous pairing between the selected DNA sequence and the selected site for integration; 3) increase efficiency of strand invasion and strand exchange between the recombining DNA sequences; 4) increase efficiency of processing of intermediate structures into mature products of recombination.

An agent which enhances homologous recombination can be introduced to a cell in a mixture which includes the double stranded DNA sequence, it can be introduced immediately prior to or after administration of the DNA sequence or it can be adhered, e.g., coated, on the DNA sequence. The entire DNA sequence can be coated with an agent which enhances homologous recombination, e.g., Rad52, e.g., hRad52, or a fragment thereof, or one or more of the ends of the DNA sequence can be coated, e.g., one or more of a protruding single stranded end of the DNA sequence can be coated. Preferably, the agent which enhances homologous recombination coats at least a portion of a protruding single stranded 3' end or 5' end of the DNA sequence.

Examples of agents which enhance homologous recombination include: Rad52 or a functional fragment thereof; Rad51 or a functional fragment thereof; Rad54 or a functional fragment thereof; or a combination or two or more of these proteins or fragments of these proteins. The agent which enhances homologous recombination can also be expressed intercellularly, e.g., a nucleic acid sequence encoding any of the above-described agents can be introduced into a cell.

A determination of whether a Rad51 fragment is functional can be made by known techniques. For example, the functionality of a Rad51 fragment can be determined based on its ability to mediate homologous pairing and strand exchange in an in vitro assay known in the art, e.g., as described in Baumann et al. (1996) *Cell* 87:757–766. Briefly, hRad51 is first preincubated with circular ssDNA and then $^{32}$P-labeled linear duplex DNA is added. The formation of joint molecules and the amount of strand exchange can be determined by electrophoresis. In addition, the functionality of a Rad51 fragment can be determined based on its ability to bind nicked duplex DNA in the presence of ATP to form helical nucleoprotein filament which can be visualized by electron microscopy as described in Benson et al. (1994) *EMBO J*. 13:5764–5771. The functionality of Rad51 can also be determined based on its ability to alleviate defects in DNA repair and homologous recombination in cells lacking functional Rad51 protein. Thus, it can be determined if a Rad51 fragment is functional if it confers a positive effect in the above-mentioned assays as compared to its absence. Moreover, the extent of the positive effect conferred by a Rad51 fragment can be compared to the extent of positive effect conferred by full-length Rad51.

The functionality of a Rad54 fragment can be determined based on its ability to hydrolyze ATP in the presence of dsDNA in an assay known in the art, e.g., a described in Swagemakers et al. (1998) *J. Biol. Chem.* 273:28292–28297. In addition, the functionality of a Rad54 fragment can be determined based on its ability to alleviate defects in DNA repair and homologous recombination in cells lacking functional Rad54 protein.

Rad52 and Functional Fragments Thereof

Rad52 provided with a DNA sequence at a selected site in a target DNA, e.g., a selected site in chromosomal DNA, can provide a higher rate of alteration of the site, e.g., homologous recombination, than would occur in its absence. While not wishing to be bound by theory, it is believed that Rad52 can provide one or more of the following functions: 1) protect the entire DNA sequence from nuclease degradation; 2) protect a protruding single stranded end of the DNA sequence, e.g., a 3' tail, from nuclease degradation; 3) increase homologous recognition between the DNA sequence and the selected site for integration; and 4) increase homologous pairing between the DNA sequence and the selected site for integration.

Rad52 can be obtained in several ways including isolation of Rad52 or expression of a sequence encoding by genetic engineering methods. For example, Van Dyke et al. (1999) *Nature* 398:728, describe production and purification of hRad52 from Sf9 cells. The nucleotide sequences of Rad52 of various species are known. See, e.g., Shen et al. (1995) *Genomics* 25(1):199–206 (murine and human Rad52); Muris et al. (1994) *Mutat. Res.* 315(3):295–305 (murine and human Rad52); Park et al. (1995) *J. Biol. Chem.* 270(26 (:15467–15470 (human Rad52).

Fragments of Rad52 can be produced in several ways, e.g., by expression of the sequence encoding Rad52 or a portion thereof or by gene activation (the preferred method), by proteolytic digestion, or by chemical synthesis. Internal or terminal fragments of Rad52 can be generated by removing one or more nucleotides from one end (for a terminal fragment) or both ends (for an internal fragment) of a nucleic acid which encodes Rad52. Expression of the mutagenized DNA produces Rad52 polypeptide fragments. Digestion with "end-nibbling" endonucleases or with various restriction enzymes can thus generate DNA's which encode an array of Rad52 fragments. DNA's which encode fragments of a Rad52 protein can also be generated by random shearing, restriction digestion or a combination of the above-discussed methods.

Rad52 fragments can also be chemically synthesized using techniques known in the art such as conventional Merrifield solid phase f-Moc or t-Boc chemistry. For example, Rad52 peptides may be arbitrarily divided into fragments of desired length with no overlap of the fragments, or divided into overlapping fragments of a desired length.

A determination of whether a Rad52 fragment is functional can be made by known techniques. For example, to determine whether a Rad52 fragment can protect against nuclease degradation, an end-labeled linearized double stranded DNA sequence, e.g., a $^{32}$P-labeled linearized double stranded DNA sequence, can be incubated with a Rad52 fragment prior to introduction of a nuclease, e.g., an exonuclease or endonuclease. The amount of released label, e.g., $^{32}$P, can then be determined. The amount of released label serves as an indicator of the ability of the Rad52 fragment to protect against nuclease degradation. In addition, the functionality of a Rad52 fragment can be determined based on its ability to stimulate the formation of joint molecules. The functionality of a Rad52 fragment can be analyzed in vitro by stimulation of hRad51-driven joint molecule formation as described in Benson et al. (1998) *Nature* 391:401–404. Briefly, hRad51 is first preincubated with circular ssDNA and then $^{32}$P-labeled linear duplex DNA is added. The formation of joint molecules can be determined by electrophoresis. The addition of Rad52 stimulates the formation of joint molecules as compared to joint molecule formation in the absence of Rad52. Thus, it can be determined if a Rad52 fragment is functional if it stimulates joint molecule formation as compared to joint molecule formation in its absence. Moreover, the extent of stimulation by a Rad52 fragment can be compared to the extent of full-length Rad52 stimulation. In addition, the functionality of a Rad52 fragment can be determined based on its ability to increase resistance to ionizing radiation and to increase rates of homologous recombination when overexpressed in cultured monkey cells as described in Park (1995) *J. Biol. Chem.* 270:15467–15470.

Agents which Inhibit Non-Homologous End Joining

An agents which inhibits non-homologous end joining can be used to provide a DNA sequence at a selected site in target DNA at a higher rate than would occur in its absence. Non-homologous end joining can lead to imprecise fusion between double stranded ends, e.g., the rejoined ends can have insertions or deletions. An agent which inhibits non-homologous end joining can be any agent which inhibits expression of and/or an activity of a molecule involved in a non-homologous end joining pathway. For example, a complex of Mre11, Rad50 and Nbs1 is involved in non-homologous end joining. Thus, for example, by inhibiting formation of this complex, e.g., by binding any of these proteins or inhibiting expression of any of these proteins, non-homologous end joining can be inhibited. In addition, other proteins involved in non-homologous end joining include Ku proteins, e.g., Ku70 or Ku80, Ligase 4 (Lig4) and Xrcc4.

Ku Inactivating Agents

Providing a Ku inactivating agent with a DNA sequence at a selected site in a target DNA, e.g., a selected site in chromosomal DNA, can provide a higher rate of alteration of the site, e.g., homologous recombination, than would occur in its absence. Ku is a heterodimer of approximately 70 kDa and 80 kDa that binds to DNA discontinuities and plays a role in double-strand break repair by non-homologous end joining. "Ku80" can also be referred to as "Ku86".

A Ku inactivating agent can inhibit Ku expression or a Ku activity. Preferably, a Ku inactivating agent interacts, e.g., binds, Ku or a nucleotide sequence encoding Ku, to inhibit Ku expression or a Ku activity. Preferably, Ku-dependent non-homologous end joining is inhibited. A Ku inhibiting agent can inhibit Ku70, Ku80 or both.

Agents which can be used to inactivate Ku include anti-Ku antibodies and Ku-binding molecules, e.g., randomly generated peptides which bind to Ku, Ku binding oligomers and polymers, and antisense Ku nucleic acid molecules. Preferably, the agent which inactivates Ku is an agent which can be administered locally such as anti-Ku antibodies and Ku-binding molecules, e.g., randomly-generated peptides which bind to Ku, and Ku binding oligomers or polymers.

Preferably, the Ku inactivating agent interacts with, e.g., binds to, Ku. Agents which interact with the Ku protein can inactivate Ku locally at the site of alteration.

For example, a Ku inactivating agent is introduced into a cell in close proximity to the DNA sequence and the targeted DNA to thereby inhibit Ku locally at the site of homologous recombination. A Ku inactivating agent can be introduced to a cell in a mixture which includes the double stranded DNA sequence, it can be introduced immediately prior to or after administration of the DNA sequence or it can be covalently linked to the DNA sequence or proteins associated with the DNA sequence, e.g., Rad52 or a fragment thereof. Cells can also be preincubated with a Ku inactivating agent such as an anti-Ku antibody or an antisense Ku nucleic acid molecule.

Anti-Ku Antibodies

An anti-Ku antibody or fragment thereof can be used to bind Ku, and thereby reduce a Ku activity. Anti-Ku antibodies can be administered such that they interact with Ku locally at the site of alteration but do not inhibit Ku expression generally in the cell. Anti-Ku antibodies include anti-Ku70 and anti-Ku80 antibodies.

A Ku protein, or a portion or fragment thereof, can be used as an immunogen to generate antibodies that bind Ku using standard techniques for polyclonal and monoclonal antibody preparation. The full-length Ku protein can be used or, alternatively, antigenic peptide fragments of Ku can be used as immunogens.

Typically, Ku or a Ku peptide is used to prepare antibodies by immunizing a suitable subject, (e.g., rabbit, goat, mouse or other mammal) with the immunogen. An appropriate immunogenic preparation can contain, for example, a Ku protein obtained by expression of the sequence encoding Ku or by gene activation, or a chemically synthesized Ku peptide. See, e.g., U.S. Pat. No. 5,460,959; and co-pending U.S. applications Ser. Nos. 08/334,797; 08/231,439; 08/334,455; and 08/928,881 which are hereby expressly incorporated by reference in their entirety. The nucleotide and amino acid sequences of Ku are known and described, for example, in Takiguchi et al. (1996) *Genomics* 35(1) :129–135. The preparation can further include an adjuvant, such as Freund's complete or incomplete adjuvant, or similar immunostimulatory agent. Immunization of a suitable subject with an immunogenic Ku preparation induces a polyclonal anti-Ku antibody response.

Anti-Ku antibodies or fragments thereof can be used as a Ku inactivating agent. Examples of anti-Ku antibody fragments include F(v), Fab, Fab' and F(ab')$_2$ fragments which can be generated by treating the antibody with an enzyme such as pepsin. The term "monoclonal antibody" or "monoclonal antibody composition", as used herein, refers to a population of antibody molecules that contain only one species of an antigen binding site capable of immunoreacting with a particular epitope of Ku. A monoclonal antibody composition thus typically displays a single binding affinity for a particular Ku protein with which it immunoreacts.

Additionally, anti-Ku antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al., *Science* 240:1041–1043, 1988; Liu et al., *PNAS* 84:3439–3443, 1987; Liu et al., *J. Immunol.* 139:3521–3526, 1987; Sun et al. *PNAS* 84:214–218, 1987; Nishimura et al., *Canc. Res.* 47:999–1005, 1987; Wood et al., *Nature* 314:446–449, 1985; and Shaw et al., *J. Natl. Cancer Inst.* 80:1553–1559, 1988); Morrison, S. L., *Science* 229:1202–1207, 1985; Oi et al., *BioTechniques* 4:214, 1986; Winter U.S. Pat. No. 5,225,539; Jones et al., *Nature* 321:552–525, 1986; Verhoeyan et al., *Science* 239:1534, 1988; and Beidler et al., *J. Immunol.* 141:4053–4060, 1988.

In addition, a human monoclonal antibody directed against Ku can be made using standard techniques. For example, human monoclonal antibodies can be generated in transgenic mice or in immune deficient mice engrafted with antibody-producing human cells. Methods of generating such mice are describe, for example, in Wood et al. PCT publication WO 91/00906, Kucherlapati et al. PCT publication WO 91/10741; Lonberg et al. PCT publication WO 92/03918; Kay et al. PCT publication WO 92/03917; Kay et al. PCT publication WO 93/12227; Kay et al. PCT publication 94/25585; Rajewsky et al. Pct publication WO 94/04667; Ditullio et al. PCT publication WO 95/17085; Lonberg, N. et al. (1994) *Nature* 368:856–859; Green, L. L. et al. (1994) *Nature Genet.* 7:13–21; Morrison, S. L. et al. (1994) *Proc. Natl. Acad. Sci. USA* 81:6851–6855; Bruggeman et al. (1993) *Year Immunol* 7:33–40; Choi et al. (1993) *Nature Genet.* 4:117–123; Tuaillon et al. (1993) *PNAS* 90:3720–3724; Bruggeman et al. (1991) *Eur J Immunol* 21:1323–1326); Duchosal et al. PCT publication WO 93/05796; U.S. Pat. No. 5,411,749; McCune et al. (1988) *Science* 241:1632–1639), Kamel-Reid et al. (1988) *Science* 242:1706; Spanopoulou (1994) *Genes & Development* 8:1030–1042; Shinkai et al. (1992) *Cell* 68:855–868). A human antibody-transgenic mouse or an immune deficient mouse engrafted with human antibody-producing cells or tissue can be immunized with Ku or an antigenic Ku peptide and splenocytes from these immunized mice can then be used to create hybridomas. Methods of hybridoma production are well known.

Human monoclonal antibodies against Ku can also be prepared by constructing a combinatorial immunoglobulin library, such as a Fab phage display library or a scFv phage display library, using immunoglobulin light chain and heavy chain cDNAs prepared from mRNA derived from lymphocytes of a subject. See, e.g., McCafferty et al. PCT publication WO 92/01047; Marks et al. (1991) *J. Mol. Biol.* 222:581–597; and Griffths et al. (1993) *EMBO J* 12:725–734. In addition, a combinatorial library of antibody variable regions can be generated by mutating a known human antibody. For example, a variable region of a human antibody known to bind Ku, can be mutated, by for example using randomly altered mutagenized oligonucleotides, to generate a library of mutated variable regions which can then be screened to bind to Ku. Methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; Barbas et al. (1992) *Proc. Nat'l Acad. Sci. USA* 89:4457–4461.

The immunoglobulin library can be expressed by a population of display packages, preferably derived from filamentous phage, to form an antibody display library. Examples of methods and reagents particularly amenable for use in generating antibody display library can be found in, for example, Ladner et al. U.S. Pat. No. 5,223,409; Kang et al. PCT publication WO 92/18619; Dower et al. PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) supra; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982. Once displayed on the surface of a display package (e.g., filamentous phage), the antibody library is screened to identify and isolate packages that express an antibody that binds Ku. In a preferred embodiment, the primary screening of the library involves panning with an immobilized Ku and display packages expressing antibodies that bind immobilized Ku are selected.

Monoclonal antibodies to Ku are also commercially available from, for example, Neomarkers (Fremont, Calif.).

Ku-Binding Molecules

Molecules which bind Ku such as Ku-binding peptides, e.g., randomly generated peptides, and Ku-binding oligomers or polymers can be used as Ku inactivating agents. Such molecules can bind to the Ku protein and thereby inhibit at least one activity of Ku such as non-homologous end-joining.

Examples of Ku-binding oligomers are set forth in WO 99/33971, the contents of which is incorporated herein by reference. Such oligomers can be composed of nucleotides, nucleotide analogs, or a combination. Preferably, the oligomers are composed of ribonucleotides. These Ku oligomers can be used to bind Ku or to identify proteins that interact with Ku. Methods of identifying Ku binding peptides using these oligomers are described in WO99/33971.

In addition, randomly generated peptides can be screened for the ability to bind Ku. For example, various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., binding to Ku, facilitates relatively easy isolation of the vector encoding the gene whose product was detected. Each of the techniques described below is amenable to high through-put analysis for screening large numbers of sequences created, e.g., by random mutagenesis techniques.

Display Libraries

In another approach to screening for Ku binding peptides, the candidate peptides are displayed on the surface of a cell or viral particle, and the ability of particular cells or viral particles to bind a Ku protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992)*J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech.* 6, 1080–1083). Surface proteins of other bacterial species have also served as peptide fusion partners. Examples include the Staphylococcus protein A and the outer membrane protease IgA of Neisseria (Hansson et al.

(1992) *J. Bacteriol.* 174, 4239–4245 and Klauser et al. (1990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are under-represented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem.* 204,357–364). To identify the sequences of the active peptides one sequences the DNA produced by the phagemid host.

Antisense Ku Nucleic Acid Sequences

Nucleic acid molecules which are antisense to a nucleotide encoding Ku can be used as an inactivating agent which inhibits Ku expression. An "antisense" nucleic acid includes a nucleotide sequence which is complementary to a "sense" nucleic acid encoding Ku, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire Ku coding strand, or to only a portion thereof. For example, an antisense nucleic acid molecule which antisense to the "coding region" of the coding strand of a nucleotide sequence encoding Ku can be used.

Given the coding strand sequences encoding Ku disclosed in, for example, Takiguchi et al. (1996) *Genomics* 35(1):129–135 and Genbank Accession Number L35932, antisense nucleic acids can be designed according to the rules of Watson and Crick base pairing. The antisense nucleic acid molecule can be complementary to the entire coding region of Ku mRNA, but more preferably is an oligonucleotide which is antisense to only a portion of the coding or noncoding region of Ku mRNA. For example, the antisense oligonucleotide can be complementary to the region surrounding the translation start site of Ku mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest.

Exogenous DNA Sequences

The DNA sequence to be provided, e.g., introduced, into the cell can alter a target sequence in a cell. For example, a selected DNA sequence can be introduced which differs from the target DNA by less than 10, 8, 5, 4, 3, 2, or by a single nucleotide, e.g., by a substitution, a deletion or an insertion. The selected DNA sequence can also differ from the target sequence by more than one nucleotide, e.g., differs from the target sequence by a number of nucleotides such that the selected DNA sequence has an unpaired region, e.g., a loop out region. These alterations can modify target sequence expression. Modified sequence expression includes: activating a sequence, e.g., a coding DNA sequence, e.g., a coding sequence normally found in a cell, which is normally silent (unexpressed) in the cell; increasing expression of a sequence, e.g., a coding DNA sequence, e.g., a coding sequence normally found in a cell, which is expressed at lower than normal levels in the cell; expressing a sequence, e.g., a coding DNA sequence, e.g., a coding sequence normally found in a cell, which is normally expressed in a defective form in the cell; changing the pattern of regulation or induction of a sequence, e.g., a coding DNA sequence, e.g., a coding sequence normally found in a cell, such that it is different than the cell's normal pattern; reducing expression of a sequence, e.g., a coding DNA sequence, e.g., a coding sequence normally found in a cell, from normal expression levels in the cell.

A selected DNA sequence can be introduced which differs from the target DNA by less than 10, 8, 5, 4, 3, 2, or by a single nucleotide, e.g., by a substitution, a deletion or an insertion. For example, the targeted sequence can differ from the wild-type sequence by less than 10, 8, 5, 4, 3, 2, or by a single nucleotide. Preferably, the targeted sequence differs from the wild-type sequence by a point mutation, e.g., a mutation arising from an insertion, deletion or substitution. Preferably, the mutation in the target sequence, e.g., a gene, is associated with, e.g., controls, a disease or a dysfunction. Examples of genes in which a mutation, e.g., a point mutation, has been associated with a disease or dysfunction include, but are not limited to, cystic fibrosis transmembrane regulator (CFTR) gene, β-globin gene, Factor VIII gene, Factor IX gene, von Willebrand factor gene, xeroderma pigmentosum group G (XP-G) gene. The selected DNA sequence for altering the target sequence can include a normal wild-type sequence which can correct the mutation. There are several genetic disorders and genes which can be altered according to the methods described herein.

In another aspect, the selected DNA sequence can also differ from the target sequence by more than one nucleotide, e.g., differs from the target sequence by a number of nucleotides such that the selected DNA sequence has an unpaired region, e.g., a loop out region. For example, the selected DNA sequence can be homologously recombined with a preselected element of the target, e.g., if one is a regulatory element and the other is a sequence which encodes a protein, the regulatory element controls expression of the protein encoding sequence. The selected DNA sequence can be a regulatory sequence, e.g., an exogenous regulatory sequence. Regulatory sequences include a promoter, an enhancer, an UAS, a scaffold-attachment region and a transcription binding site. In addition, the selected DNA sequence can also include an exon, an intron, a CAP site, a nucleotide sequence ATG, a marker, e.g., a selection marker, a splice-donor site and/or encoding DNA in frame with the target sequence. The selected DNA sequence can also include a coding region, e.g., DNA sequence encoding a protein.

The coding sequence can be endogenous, e.g., the selected DNA sequence is a regulatory sequence, or the selected DNA sequence can include the coding region, i.e., the coding region is exogenous. The coding region can encode various proteins. Examples of such proteins include: erythropoietin, calcitonin, growth hormone, insulin, insulinotropin, insulin-like growth factors, parathyroid hormone, α2-interferon (IFNA2), β-interferon, γ-interferon, nerve growth factors, FSHβ, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-granulocyte (GCSF), CSF-macrophage, CSF-granulocyte/macrophage, immunoglobulins, catalytic antibodies, protein kinase C, glucocerebrosidase, superoxide dismutase, tissue plasminogen activator, urokinase, antithrombin III, DNAse, α-galactosidase, tyrosine hydroxylase, blood clotting factor V, blood clotting factor VII, blood clotting factor VIII, blood clotting factor IX, blood clotting factor X, blood clotting factor XIII, apolipoprotein E, apolipoprotein A-I, globins, low density lipoprotein receptor, IL-2 receptor, IL-2 antagonists, α-1-antitrypsin, immune response modifiers, β-glucoceramidase, α-iduronidase, α-L-iduronidase, glucosamine-N-sulfatase, α-N-acetylglucosaminidase, acetylcoenzymeA:α-glucosamine-N-acetyltransferase, N-acetylglucosamine-6-sulfatase, β-galactosidase, β-glucuronidase, N-acetylgalactosamine-6-sulfatase, and soluble CD4. Sequences encoding these proteins are known.

The term exogenous refers to a sequence which is introduced into a cell by the methods described herein. The exogenous sequence can have a sequence identical or different from an endogenous sequence present in the cell.

Preferably, the DNA sequence is a linear sequence.

Targeting Sequence or Sequences

Targeting sequence or sequences are DNA sequences which permit homologous recombination into the genome of a cell containing the targeted sequence, e.g., the targeted gene. The term "targeting sequence" and "flanking sequence" are used interchangeably herein. Targeting sequences are, generally, DNA sequences which are homologous to (i.e., identical or sufficiently similar to cellular DNA such that the targeting sequence and cellular DNA can undergo homologous recombination) DNA sequences normally present in the genome of a cells as obtained. For example, the targeting sequence can be sufficiently homologous to: coding or noncoding DNA, a sequence lying upstream of the transcriptional start site, within, or downstream of the transcriptional stop site of a gene of interest, or sequences present in the genome through a previous modification. The targeting sequence or sequences used are selected with reference to the site into which the selected DNA sequence is to be inserted or the site into which the targeted sequence is to be altered.

One or more targeting sequences can be employed. Preferably, the selected DNA sequence is flanked by two targeting sequences. A targeting sequence can be within a gene or coding sequence (such as, the sequences of an exon and/or intron), immediately adjacent to a coding sequence of a gene (e.g., with less than 10, 5, 4, 3, 2, 1 or no additional nucleotides between the targeting sequence and the coding region of the gene), upstream of a coding sequence of a gene (such as the sequences of the upstream non-coding region or endogenous promoter sequences), or upstream of and at a distance from the coding sequence of a gene (such as, sequences upstream of the endogenous promoter). The targeting sequence or sequences can include those regions of the targeted sequence presently known or sequenced and/or regions further upstream which are structurally uncharacterized but can be mapped using restriction enzymes and determined by one skilled in the art.

A targeting sequence can be used to insert a DNA sequence which includes a regulatory sequence immediately adjacent to, upstream, or at a substantial distance from the coding sequence of an endogenous gene. Alternatively or additionally, sequences which affect the structure or stability of the RNA or protein produced can be replaced, removed, added, or otherwise modified by targeting. For example, RNA stability elements, splice sites, and/or leader sequences of RNA molecules can be modified to improve or alter the function, stability, and/or translatability of an RNA molecule. Protein sequences may also be altered, such as signal sequences, propeptide sequences, active sites, and/or structural sequences for enhancing or modifying transport, secretion, or functional properties of a protein. A protein sequence can also be altered, e.g., corrected, by targeting a site in the gene encoding the protein which includes a mutation, e.g., a point mutation.

In one aspect, the targeting sequence can be homologous to a portion of human follicle stimulating hormone β(FSHβ). FSH is a gonadotrophin which plays an essential role in the maintenance and development of oocytes and spermatozoa in normal reproductive physiology. FSH includes two subunits, α and β, the latter being responsible for FSH's biological specificity. The target site to which a given targeting sequence is homologous can reside within an exon and/or intron of the FSHβ gene, upstream of and immediately adjacent to the FSHβ-coding region, or upstream of and at a distance from the FSHβ-coding region. For example, the first of the two targeting sequences (or the entire targeting sequence, if there is only one targeting sequence in the construct) can be derived from the genomic regions upstream of the FSHβ-coding sequences. For example, this targeting sequence can include a portion of SEQ ID NO: 1, e.g., at least 20, 30, 50, 100, or 1000 consecutive nucleotides from the sequence corresponding to positions −7,454 to −1,417 (SEQ ID NO:2) or to positions −696 to −155 (SEQ ID NO:3). The second of the two targeting sequences can target a genomic region upstream of the coding sequence (e.g., also contain a portion of SEQ ID NO:2 or 3), or target an exon or intron of the gene. Sequences which can be used to target FSHβ are further described in U.S. Ser. No. 09/305,639, the contents of which is incorporated herein in its entirety.

The targeting sequence can be homologous to a portion of human interferon-α2 (IFNα2). Interferon-α constitutes a complex gene family with 14 genes clustered on the short arm of chromosome 9. None of these genes, including IFNα2 gene, have introns. Interferon-α is produced by macrophages, T cells and B cells as wells as many other cell types. Interferon-α has considerable anti-viral effects, and has been shown to be efficacious in treating infections by papilloma virus, hepatitis B and C viruses, vaccina, herpes simplex virus, herpes zoster varicellosus virus and rhinovirus.

The target site to which a given targeting sequence is homologous can reside within the coding region of the IFNα2 gene, upstream of and immediately adjacent to the coding region, or upstream and at a distance from the coding region. For example, the first of the two targeting sequences (or the entire targeting sequence, if there is only one targeting sequence in the construct) can be derived from the genomic regions upstream of the IFNα2-coding sequences. For example, this targeting sequence can include a portion (e.g., at least 20, 50, 100 or 1000 consecutive nucleotides) of SEQ ID NO:4, which corresponds to nucleotides −4074 to −511 of the IFNα2 gene. The second of the two targeting sequences may target a genomic region upstream of the coding sequence itself. By way of example, the second targeting sequence may contain at its 3' end, an exogenous coding region identical to the first few codons of the IFNα2 coding sequence. Upon homologous recombination, the exogenous coding region recombines with the targeted part of the endogenous IFNα2 coding sequence. Sequences which can be used to target IFNα2 are further described in U.S. Ser. No. 09/305,638, the contents of which is incorporated herein in its entirety.

In another aspect, the targeting sequence can be homologous to a portion of human granulocyte colony-stimulating factor (GCSF). GCSF is a cytokine that stimulates the proliferation and differentiation of hematopoietic progenitor cells committed to the neutrophil/granulocyte lineage. GCSF is routinely used in the prevention of chemotherapy-induced neutropenia and in association with bone marrow transplantation. Chronic idiopathic and congenital neutropenic disorders also show improvement after GCSF injection. The target site to which a given targeting sequence is homologous can reside within an exon and/or intron of the GCSF gene, upstream of and immediately adjacent to the GCSF coding region, or upstream of and at a distance from the GCSF coding region.

For example, the first of the two targeting sequences in the construct (or the entire targeting sequence, if there is only one targeting sequence in the construct) can be homologous to the genomic regions upstream of the GCSF-coding sequences. For example, this targeting sequence can contain a portion of SEQ ID NO:5, which corresponds to nucleotides −6,578 to 101 of human GCSF gene (e.g., at least 20, 50, 100, or 1000 consecutive nucleotides from the sequence corresponding to positions −6,578 to −364 (SEQ ID NO:6)). The second of the two targeting sequences in the construct may target a genomic region upstream of the coding sequence (e.g., also contain a portion of SEQ ID NO:6), or target an exon or intron of the gene. Sequences which can be used to target GCSF are further described in U.S. Ser. No. 09/305,384, the contents of which is incorporated herein in its entirety.

Regulatory Sequence

A DNA sequence can include a regulatory sequence. The regulatory sequence can include one or more promoters (such as a constitutive or inducible promoter), enhancers, an UAS, scaffold-attachment regions or matrix attachment sites, negative regulatory elements, transcription factor binding sites, or combinations of these sequences.

The regulatory sequence can contain an inducible promoter such that cells as produced or as introduced into an individual can be induced to express a product, e.g., the cell does not express the product but can be induced to express it. The regulatory sequence can contain an inducible promoter such that the product is expressed upon introduction of the regulatory sequence. The regulatory sequence can be a cellular or viral sequence. Such regulatory sequences include, but are not limited to, those that regulate the expression of SV40 early or late genes, adenovirus major late genes, the mouse metallothionein-I gene, the elongation factor-1α gene, cytomegalovirus genes, collagen genes, actin genes, immunoglobulin genes, γ actin gene, transcription activator YY1 gene, fibronectin gene, or the HMG-CoA reductase gene. The regulatory sequence can further contain a transcription factor binding site, such as a TATA Box, CCAAT Box, AP1, Sp1 or NF-κB binding site.

Additional DNA Sequence Elements

The DNA sequence can further include one or more exons. An exon is a DNA sequence which is copied into RNA and is present in a mature mRNA molecule. An exons can contain DNA which encodes one or more amino acids and/or partially encodes an amino acid (i.e., one or two bases of a codon). Alternatively, an exon contains DNA which corresponds to a non-coding region, e.g., a 5' non-coding region. Where the exogenous exon or exons encode one or more amino acids and/or a portion of an amino acid, the DNA sequence can be designed such that, upon transcription and splicing, the reading frame is in-frame with the second exon or coding region of a targeted gene. As used herein, in-frame means that the encoding sequences of a first exon and a second exon, when fused, join together nucleotides in a manner that does not change the appropriate reading frame of the portion of the mRNA derived from the second exon.

If the first exon of the targeted gene contains the sequence ATG to initiate translation, the exogenous exon preferably contains an ATG. In addition, an exogenous exon containing an ATG can further include one or more nucleotides such that the resulting coding region of the mRNA including the second and subsequent exons of the targeted gene is in-frame. Examples of such targeted genes in which the first exon contains an ATG include the genes encoding human erythropoietin, human growth hormone, human colony stimulating factor-granulocyte/macrophage (hGM-CSF), and human colony stimulating factor-granulocyte (hG-CSF).

A splice-donor site is a sequence which directs the splicing of one exon to another exon. Typically, a first exon lies 5' of a second exon, and a splice-donor site overlapping and flanking the first exon on its 3' side recognizes a splice-acceptor site flanking the second exon on the 5' side of the second exon. A splice-donor site can have a characteristic consensus sequence represented as: (A/C)AG GURAGU (where R denotes a purine nucleotide) with the GU in the fourth and fifth positions, being required (Jackson 1991) *Nucleic Acids Res.* 19: 3715–3798). The first three bases of the splice-donor consensus site are the last three bases of the exon. Splice-donor sites can be functionally defined by their ability to effect the appropriate reaction within the mRNA splicing pathway.

An unpaired splice-donor site is a splice-donor site which is present in a targeted sequence and is not accompanied in the DNA sequence by a splice-acceptor site positioned 3' to the unpaired splice-donor site. The unpaired splice-donor site can result in splicing to an endogenous splice-acceptor site.

A splice-acceptor site is a sequence which, like a splice-donor site, directs the splicing of one exon to another exon. Acting in conjunction with a splice-donor site, the splicing apparatus uses a splice-acceptor site to effect the removal of an intron. Splice-acceptor sites can have a characteristic sequence represented as: YYYYYYYYYYNYAG (SEQ ID NO:10), where Y denotes any pyrimidine and N denotes any nucleotide (Jackson (1991) *Nucleic Acids Res.* 19:3715–3798).

An intron is defined as a sequence of one or more nucleotides lying between two exons and which is removed, by splicing, from a precursor RNA molecule in the formation of an mRNA molecule.

The regulatory sequence can be linked to an ATG start codon, for initiating translation. Optionally, a CAP site (a specific mRNA initiation site which is associated with and utilized by the regulatory region) can be linked to the regulatory sequence and the ATG start codon. Alternatively, the CAP site associated with and utilized by the regulatory sequence is not included in the target sequence, and the transcriptional apparatus provides a new CAP site. A CAP site can usually be found approximately 25 nucleotides 3' of the TATA box. A splice-donor site can be placed immediately adjacent to an ATG, e.g., where the presence of one or more nucleotides is not required for the exogenous exon to be in-frame with the second exon of the targeted gene. DNA encoding one or more amino acids or portions of an amino acid in-frame with the coding sequence of the targeted gene, can be placed immediately adjacent to the ATG on its 3' side. As such, the splice-donor site can be placed immediately adjacent to the encoding DNA on its 3' side.

An encoding portion of a DNA sequence (e.g., in exon 1 of the DNA sequence) can encode one or more amino acids, and/or a portion of an amino acid, which are the same as those of the endogenous protein. For example, the encoding DNA sequence can correspond to the first exon of the gene of interest. The encoding DNA can alternatively encode one or more amino acids or a portion of an amino acid different from the first exon of the protein of interest, for example, where the amino acids of the first exon of the protein of interest are not critical to the activity or activities of the protein. For example, when fusions to an endogenous human erythropoietin (EPO) gene are constructed, sequences encoding the first exon of human growth hormone (hGH) can be employed. In this example, fusion of hGH exon 1 to EPO exon 2 results in the formation of a hybrid signal peptide which is functional. However, any exon of human or non-human origin in which the encoded amino acids do not prevent the function of the hybrid signal peptide can be used.

Where the desired product is a fusion protein of the endogenous protein and encoding sequences in the DNA sequence, the exogenous encoding DNA incorporated into the cells can include DNA which encodes one or more exons or a sequence of cDNA corresponding to a translation or transcription product which is to be fused to the product of the endogenous targeted gene. Thus, targeting can be used to prepare chimeric or multifunctional proteins which combine structural, enzymatic, or ligand or receptor binding properties from two or more proteins into one polypeptide. For example, the exogenous DNA sequence can encode, e.g., an anchor to the membrane for the targeted protein or a signal peptide to provide or improve cellular secretion, leader sequences, enzymatic regions, transmembrane domain regions, co-factor binding regions or other functional regions. Examples of proteins which are not normally secreted, but which could be fused to a signal protein to provide secretion include dopa-decarboxylase, transcriptional regulatory proteins and tyrosine hydroxylase.

The DNA sequence can be obtained from sources in which it occurs in nature or can be produced, using genetic engineering techniques or synthetic processes.

Target Sequence

The DNA sequence, when transfected into cells, such as primary, secondary or immortalized cells, can control the expression of a desired product for example, the active or, functional portion of the protein or RNA. The DNA sequence can also encode a desired product. The product can be, for example, a hormone, a cytokine, an antigen, an antibody, an enzyme, a clotting factor, a transport protein, a receptor, a regulatory protein, a structural protein, a transcription factor, an anti-sense RNA, or a ribozyme. Additionally, the product can be a protein or a nucleic acid which does not occur in nature (i.e., a fusion protein or nucleic acid).

Such products include erythropoietin, calcitonin, growth hormone, insulin, insulinotropin, insulin-like growth factors, parathyroid hormone, interferon β, and interferon γ, nerve growth factors, FSHβ, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-granulocyte, CSF-macrophage, CSF-granulocyte/macrophage, immunoglobulins, catalytic antibodies, protein kinase C, glucocerebrosidase, superoxide dismutase, tissue plasminogen activator, urokinase, antithrombin III, DNAse, α-galactosidase, tyrosine hydroxylase, blood clotting factors V, blood clotting factor VII, blood clotting factor VIII, blood clotting factor IX, blood clotting factor X, blood clotting factor XIII, apolipoprotein E or apolipoprotein A-I, globins, low density lipoprotein receptor, IL-2 receptor, IL-2 antagonists, alpha-1 anti-trypsin, immune response modifiers, β-glucoceromidase, α-iduronidase, αL-iduronidase, glucosamine-N-sulfatase, α-N-acetylglucosaminidase, acetylcoenzymeA:α-glucosamide-N-acetyltransferase, N-acetylglucosamine-6-sulfatase, β-galactosidase, β-glucuronidase, N-acetylgalactosamine-6-sulfatase, and soluble CD4.

Selectable Markers and Amplification

The identification of the targeting event can be facilitated by the use of one or more selectable marker genes. These markers can be included in the DNA sequence or can be present on a different construct. Selectable markers can be divided into two categories: positively selectable and negatively selectable (in other words, markers for either positive selection or negative selection). In positive selection, cells expressing the positively selectable marker are capable of surviving treatment with a selective agent (such as neo, xanthine-guanine phosphoribosyl transferase (gpt), dhfr, adenine deaminase (ada), puromycin (pac), hygromycin (hyg), CAD which encodes carbamyl phosphate synthase, aspartate transcarbamylase, and dihydro-orotase glutamine synthetase (GS), multidrug resistance 1 (mdrl) and histidine D (hisD), allowing for the selection of cells in which the targeting construct integrated into the host cell genome. In negative selection, cells expressing the negatively selectable marker are destroyed in the presence of the selective agent. The identification of the targeting event can be facilitated by the use of one or more marker genes exhibiting the property of negative selection, such that the negatively selectable marker is linked to the exogenous DNA sequence, but configured such that the negatively selectable marker flanks the targeting sequence, and such that a correct homologous recombination event with sequences in the host cell genome does not result in the stable integration of the negatively selectable marker (Mansour et al. (1988) *Nature* 336:348–352). Markers useful for this purpose include the Herpes Simplex Virus thymidine kinase (TK) gene, the bacterial gpt gene, diphteria toxin and antisense RNA or ribozyme for mRNA that codes for a gene essential for cell survival.

A variety of selectable markers can be incorporated into primary, secondary or immortalized cells. For example, a selectable marker which confers a selectable phenotype such as drug resistance, nutritional auxotrophy, resistance to a cytotoxic agent or expression of a surface protein, can be used. Selectable marker genes which can be used include neo, gpt, dhfr, ada, pac, hyg, CAD, GS, mdr1 and hisD. The selectable phenotype conferred makes it possible to identify and isolate recipient cells.

Genes encoding selectable markers (e.g., ada, GS, dhfr and the multifunctional CAD gene) have the added characteristic that they enable the selection of cells containing increased copies of the selectable marker and flanking the genomic sequence. This feature provides a mechanism for significantly increasing the copy number of an adjacent or linked gene for which increased copies is desirable. Mutated versions of these sequences showing improved selection properties and other sequences leading to increased copies can also be used.

The order and number of components in the DNA sequence can vary. For example, the order can be: a first targeting sequence—selectable marker—regulatory sequence—an exon—a splice-donor site—a second targeting sequence or, in the alternative, a first targeting sequence—regulatory sequence—an exon—a splice-donor site—DNA encoding a selectable marker—a second targeting sequence. Cells that stably integrate the construct will survive treatment with the selective agent; a subset of the stably transfected cells will be homologously recombinant cells. The homologously recombinant cells can be identified by a variety of techniques, including PCR, Southern hybridization and phenotypic screening. The order of the construct can be: a first targeting sequence—selectable marker—regulatory sequence—an exon—a splice-donor site—an intron—a splice-acceptor site—a second targeting sequence.

Alternatively, the order of components in the DNA sequence can be, for example: a first targeting sequence—selectable marker 1—regulatory sequence—an exon—a splice-donor site—a second targeting sequence—selectable marker 2, or, alternatively, a first targeting sequence—regulatory sequence—an exon—a splice-donor site—selectable marker 1—a second targeting sequence—selectable marker 2. In this arrangement, selectable marker 2 can display the property of negative selection. That is, the gene product of selectable marker 2 can be selected against by growth in an appropriate media formulation containing an agent (typically a drug or metabolite analog) which kills cells expressing selectable marker 2. Recombination between the targeting sequences flanking selectable marker 1 with homologous sequences in the host cell genome results in the targeted integration of selectable marker 1, while selectable marker 2 is not integrated. Such recombination events generate cells which are stably transfected with selectable marker 1 but not stably transfected with selectable marker 2, and such cells can be selected for by growth in the media containing the selective agent which selects for selectable marker 1 and the selective agent which selects against selectable marker 2.

The DNA sequence also can include a positively selectable marker that allows for the selection of cells containing increased copies of that marker. The increased copies of such a marker result in the co-amplification of flanking DNA sequences. For example, the order of components can be: a first targeting sequence—a positively selectable marker which increases the number of copies—a second selectable marker (optional)—regulatory sequence—an exon—a splice-donor site—a second targeting DNA sequence. The activated gene can be further increased by the inclusion of a selectable marker gene which has the property that cells containing increased copies of the selectable marker gene can be selected for by culturing the cells in the presence of the appropriate selectable agent. The activated endogenous gene will be increases in tandem with the selectable marker gene. Cells containing many copies of the activated endogenous gene may produce very high levels of the desired protein and are useful for in vitro protein production and gene therapy.

The selectable and other marker genes do not have to lie immediately adjacent to each other.

DNA Sequence/Homologous Recombination Enhancing Agent/Non-Homologous End Joining Inhibiting Agent Complexes Homologous recombination between a double stranded DNA sequence and a selected target DNA, e.g., chromosomal DNA in a cell, can be promoted by providing an agent which enhances homologous recombination, e.g., a Rad52 protein, and an agent which inhibits non-homologous end joining, e.g., a Ku inactivating agent (e.g., a anti-Ku antibody), in sufficiently close proximity to the DNA sequence and the targeted site. "Sufficiently close proximity" as used herein refers to introduction of a homologous recombination enhancing agent or an agent which inhibits non-homologous end joining or both such that the concentration of the homologous recombination enhancing agent and/or agent which inhibits non-homologous end joining is sufficient to provide a higher rate of an alteration at a targeted site, e.g., homologous recombination between a DNA sequence and a target sequence. Several methods can be used to provide the introduction of the DNA sequence, homologous recombination enhancing agent, and an agent which inhibits non-homologous end joining within close proximity of each other. By administering these compounds in close proximity of each other and the target DNA, the activity of compounds such as Rad52 and Ku inactivating molecules, e.g., an anti-Ku antibody, are localized at the site of homologous recombination. For example, local inhibition of Ku activity may be preferable over whole cell inhibition of Ku activities.

The close proximity of the DNA sequence, a homologous recombination enhancing agent, and an agent which inhibits non-homologous end joining can be maintained by introducing these elements as part of a complex. For example, DNA-protein complexes can be used. The core of a DNA-protein complex can be composed of the double stranded DNA sequence which is to be introduced into the selected site in the target DNA. A homologous recombination enhancing agent, e.g., a Rad52 protein or fragment thereof, can be adhered, e.g., coated, on the DNA sequence, e.g., on the entire sequence or just the ends of the DNA sequence, e.g., on at least a portion of a single stranded protruding end of the DNA sequence. The DNA-protein complex can further include an agent which inhibits non-homologous end joining, e.g., a Ku inactivating agent such as an anti-Ku antibody, which is covalently linked to either the DNA sequence or to the homologous recombination enhancing agent. The agent which inhibits non-homologous end joining can also be non-covalently linked to the DNA sequence or to the homologous recombination enhancing agent.

The compounds can also be maintained in close proximity to one another by providing the DNA sequence, the homologous recombination enhancing agent and the agent which inhibits non-homologous end joining in a liposome or vesicle. For example, liposomal suspensions can also be used as pharmaceutically acceptable carriers of these elements. Liposomal suspensions can be prepared according to methods known to those skilled in the art, for example, as described in U.S. Pat. No. 4,522,811.

The DNA sequence, the homologous recombination enhancing agent and the agent which inhibits non-homologous end joining can also be part of a mixed solution which can be microinjected into a cell or each of these compounds can be introduced in quick succession to the others such that all three of these compounds are present in the cell at the same time. Other methods of introducing one or more of these compounds include receptor-mediated delivery, electroporation and calcium phosphate precipitation.

Cells

Primary and secondary cells to be transfected can be obtained from a variety of tissues and include cell types which can be maintained and propagated in culture. For example, primary and secondary cells which can be transfected include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Primary cells are preferably obtained from the individual to whom the transfected primary or secondary cells are administered (i.e., an autologous cell). However, primary cells may be obtained from a donor (other than the recipient) of the same species (i.e., an allogeneic cell) or another species (i.e., a xenogeneic cell) (e.g., mouse, rat, rabbit, cat, dog, pig, cow, bird, sheep, goat, horse).

Primary or secondary cells of vertebrate, particularly mammalian, origin can be transfected with an exogenous DNA sequence, e.g., an exogenous DNA sequence encoding a therapeutic protein, and produce an encoded therapeutic protein stably and reproducibly, both in vitro and in vivo, over extended periods of time. In addition, the transfected primary and secondary cells can express the encoded product in vivo at physiologically relevant levels, cells can be recovered after implantation and, upon reculturing, to grow and display their preimplantation properties.

Alternatively, primary or secondary cells of vertebrate, particularly mammalian, origin can be transfected with an exogenous DNA sequence which includes a regulatory sequence. Examples of such regulatory sequences include one or more of: a promoter, an enhancer, an UAS, a scaffold attachment region or a transcription binding site. The targeting event can result in the insertion of the regulatory sequence of the DNA sequence, placing a targeted endogenous gene under their control (for example, by insertion of either a promoter or an enhancer, or both, upstream of the endogenous gene or regulatory region). Optionally, the targeting event can simultaneously result in the deletion of an endogenous regulatory sequence, such as the deletion of a tissue-specific negative regulatory sequence, of a gene. The targeting event can replace an existing regulatory sequence; for example, a tissue-specific enhancer can be replaced by an enhancer that has broader or different cell-type specificity than the naturally-occurring elements, or displays a pattern of regulation or induction that is different from the corresponding nontransfected cell. In this regard, the naturally occurring sequences are deleted and new sequences are added. Alternatively, the endogenous regulatory sequences are not removed or replaced but are disrupted or disabled by the targeting event, such as by targeting the exogenous sequences within the endogenous regulatory elements. Introduction of a regulatory sequence by homologous recombination can result in primary or secondary cells expressing a therapeutic protein which it does not normally express. In addition, targeted introduction of a regulatory sequence can be used for cells which make or contain the therapeutic protein but in lower quantities than normal (in quantities less than the physiologically normal lower level) or in defective form, and for cells which make the therapeutic protein at physiologically normal levels, but are to be augmented or enhanced in their content or production.

The transfected primary or secondary cells may also include a DNA sequence encoding a selectable marker which confers a selectable phenotype upon them, facilitating their identification and isolation. Methods for producing transfected primary, secondary cells which stably express the DNA sequence, clonal cell strains and heterogenous cell strains of such transfected cells, methods of producing the clonal and heterogenous cell strains, and methods of treating or preventing an abnormal or undesirable condition through the use of populations of transfected primary or secondary cells are part of the invention.

Transfection of Primary or Secondary Cells, Homologous Recombination and Production of Clonal or Heterogenous Cell Strains Vertebrate tissue can be obtained by standard methods such as punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate and resuspended before transfection is carried out. Primary cells or secondary cells are combined with the DNA sequence to be introduced into their genomes which optionally includes DNA encoding a selectable marker, and treated in order to accomplish transfection. In addition, the primary or secondary cells are combined with a Rad52 protein or fragment thereof and a Ku-inactivating molecule, e.g., an anti-Ku antibody, either alone or as part of a complex.

Transfected primary or secondary cells, can be made by electrophoration. Electrophoration is carried out at appropriate voltage and capacitance (and corresponding time constant) to result in entry of the DNA construct(s) into the primary or secondary cells. Electroporation can be carried out over a wide range of voltages (e.g., 50 to 2000 volts) and corresponding capacitance. Total DNA of approximately 0.1 to 500 $\mu$g is generally used.

Preferably, primary or secondary cells are transfected using microinjection. Alternatively, known methods such as calcium phosphate precipitation, modified calcium phosphate precipitation and polybrene precipitation, liposome fusion and receptor-mediated gene delivery can be used to transfect cells. A stably, transfected cell is isolated and cultured and subcultivated, under culturing conditions and for sufficient time, to propagate the stably transfected secondary cells and produce a clonal cell strain of transfected secondary cells. Alternatively, more than one transfected cell is cultured and subculturated, resulting in production of a heterogenous cell strain.

After transfection, the cell is maintained under conditions which permit homologous recombination, as is known in the art (Capecchi (1989) *Science* 244:1288–1292.

Homologously recombinant primary or secondary cells can undergo a sufficient number of doublings to produce either a clonal cell strain or a heterogenous cell strain of sufficient size to provide the therapeutic protein to an individual in effective amounts. In general, for example, 0.1 cm$^2$ of skin is biopsied and assumed to contain 100,000 cells; one cell is used to produce a clonal cell strain and undergoes approximately 27 doublings to produce 100 million homologously recombinant secondary cells. If a heterogenous cell strain is to be produced from an original homologously recombinant population of approximately 100,000 cells, only 10 doublings are needed to produce 100 million cells.

The number of required cells in a homologously recombinant clonal or heterogenous cell strain is variable and depends on a variety of factors, including but not limited to, the use of the homologously recombinant cells, the functional level of the exogenous DNA sequence in the cells, the functional level of altered DNA sequence in the cell, the site of implantation of the homologously recombinant cells (for example, the number of cells that can be used is limited by the anatomical site of implantation), and the age, surface area, and clinical condition of the patient. To put these factors in perspective, to deliver therapeutic levels of human growth hormone in an otherwise healthy 10 kg patient with isolated growth hormone deficiency, approximately one to five hundred million homologously recombinant fibroblasts would be necessary (the volume of these cells is about that of the very tip of the patient's thumb).

Several methods can be used to determine the efficacy of the methods described herein to enhance homologous recombination in a cell. For example, an experimental system can be designed to detect a non-conservative substitution in a cell, e.g., a human cell. The substitution can be a C to T substitution at the CGA codon of exon 3 of the HPRT gene, which is part of an XhoI site. This mutation creates a TGA termination signal which results in a HPRT-negative phenotype scored as resistant to 6-thioguanine (6-TG). This mutation is also accompanied by a loss of the corresponding XhoI site. Briefly, a DNA sequence which includes the C to T substitution can be introduced by microinjection into a human fibroblast cell as part of a complex which includes an agent which enhances homologous recombination and an agent which inactivates Ku. The cells are cultured and allowed to propagate prior to introducing the cells onto media which includes 6-TG. 6-TG resistant clones can then be scored to determine the presence of the mutated DNA sequence. The presence of a homologous recombination event can be detected by Southern blot analysis of XhoI digested genomic DNA using an HPRT-specific probe. The results can also be compared to control cells in which the mutated DNA sequence is introduced in the absence of an agent which enhances homologous recombination and an agent which inactivates Ku.

Implantation of Clonal Cell Strain or Heterogenous Cell Strain of Homologously Recombinant Secondary Cells The homologously recombinant cells produced as described above can be introduced into an individual to whom the therapeutic protein is to be delivered, using known methods. The clonal cell strain or heterogenous cell strain is then introduced into an individual, using known methods, using various routes of administration and at various sites (e.g., renal subcapsular, subcutaneous, central nervous system (including intrathecal), intravascular, intrahepatic, intrasplanchnic, intraperitoneal (including intraomental), or intramuscular implantation). Once implanted in the individual, the homologously recombinant cells produce the therapeutic product encoded by the exogenous synthetic DNA or the homologously recombinant cells express a therapeutic protein encoded by an endogenous DNA sequence under the control of an exogenous regulatory sequence. For example, an individual who has been diagnosed with Hemophilia B, a bleeding disorder that is caused by a deficiency in Factor IX, a protein normally found in the blood, is a candidate for a gene therapy cure. The patient has a small skin biopsy performed; this is a simple procedure which can be performed on an out-patient basis. The piece of skin, approximately the size of a matchhead, is taken, for example, from under the arm and requires about one minute to remove. The sample is processed, resulting in isolation of the patient's cells (in this case, fibroblasts) and genetically engineered to produce the missing Factor IX. Based on the age, weight, and clinical condition of the patient, the required number of cells are grown in large-scale culture. The entire process should require 4–6 weeks and, at the end of that time, the appropriate number of genetically-engineered cells are introduced into the individual, once again as an outpatient (e.g., by injecting them back under the patient's skin). The patient is now capable of producing his or her own Factor IX and is no longer a hemophiliac.

A similar approach can be used to treat other conditions or diseases. For example, short stature can be treated by administering human growth hormone to an individual by implanting primary or secondary cells which express human growth hormone.

As this example suggests, the cells used will generally be patient-specific genetically-engineered cells. It is possible, however, to obtain cells from another individual of the same species or from a different species. Use of such cells might require administration of an immunosuppressant, alteration of histocompatibility antigens, or use of a barrier device to prevent rejection of the implanted cells.

For many diseases, this will be a one-time treatment and, for others, multiple gene therapy treatments will be required.

Transfected primary or secondary cells can be administered alone or in conjunction with a barrier or agent for inhibiting immune response against the cell in a recipient subject. For example, an immunosuppressive agent can be administered to a subject inhibit or interfere with normal response in the subject. Preferably, the immunosuppressive agent is an immunosuppressive drug which inhibits T cell/or B cell activity in a subject. Examples of such immunosuppressive drugs commercially available (e.g., cyclosporin A is commercially available from Sandoz Corp. East Hanover, N.J.).

An immunosuppressive agent e.g., drug, can be administered to a subject at a dosage sufficient to achieve the desired therapeutic effect (e.g., inhibition of rejection of the cells). Dosage ranges for immunosuppressive drugs are known in the art. See, e.g., Freed et al. (1992) *N. Engl. J. Med.* 327:1549; Spencer et al. (1992) *N. Engl. J. Med.* 327:1541' Widner et al. (1992) *n. Engl. J. Med* 327:1556). Dosage values may vary according to factors such as the disease state, age, sex, and weight of the individual.

Another agent with can be used to inhibit T cell activity in a subject is an antibody, or fragment of derivative thereof. Antibodies capable of depleting or sequestering T cells in vivo are known in the art. Polyclonal antisera can be used, for example, anti-lymphocyte serum. Alternatively, one or more monoclonal antibodies can be used. Preferred T cell depleting antibodies include monoclonal antibodies which bind to CD2, CD3, CD4, CD8, CD40, CD40, ligand on the cell surface. Such antibodies are known in the art and are commercially available, for example, form American Type Culture Collection. A preferred antibody for binding CD3 on human T cells is OKT3 (ATCC CRL 8001).

An antibody which depletes, sequesters or inhibits T cells within a recipient subject can be administered in a dose for an appropriate time to inhibit rejection of cells upon transplantation. Antibodies are preferably administered intravenously in a pharmaceutically acceptable carrier of diluent (e.g., saline solution).

Another way of interfering with or inhibiting an immune response to the cells in a recipient subject is to use an immunobarrier. An "immunobarrier" as used herein, refers to a device which serves as a barrier between the administered cell and cells involved in immune response in a subject. For example, the cells can be administered in an implantable device. An implantable device can include the cells contained within a semi-permeable barrier, i.e., one which lets nutrients and the product diffuse in and out of the barrier but which prevents entry or larger immune system components, e.g., antibodies or complement. An implant able device typically includes a matrix, e.g., a hydrogel, or core in which cells are disposed. Optionally, a semi permeable coating can enclose the gel. If disposed within the gel core, the administered cells should be sequestered from the cells of the immune system and should be cloaked from the cells and cytotoxic antibodies of the host. Preferably, a permselective coating such as PLL or PLO is used. The coating often has a porosity which prevents components of the recipient's immune system from entering and destroying the cells within the implantable device.

Many methods for encapsulating cells are known in the art. For example, encapsulation using a water soluble gum to obtain a semi-permeable water insoluble gel to encapsulate cells for production and other methods of encapsulation are disclosed in U.S. Pat. No. 4,352,883. Other implantable devices which can be used are disclosed in U.S. Pat. Nos. 5,084,350, 5,427,935, WO 95/19743 published Jul. 27, 1995, U.S. Pat. Nos. 5,545,423, 4,409,331, 4,663,286, and European Patent No. 301,777.

Uses of Homologously Recombinant Primary and Secondary Cells and Cell Strains

Homologously recombinant primary or secondary cells or cell strains have wide applicability as a vehicle or delivery system for therapeutic proteins, such as enzymes, hormones, cytokines, antigens, antibodies, clotting factors, anti-sense RNA, regulatory proteins, transcription proteins, receptors, structural proteins, novel (non-optimized) proteins and nucleic acid products, and engineered DNA. For example, homologously recombinant primary or secondary cells can be used to supply a therapeutic protein, including, but not limited to, erythropoietin, calcitonin, growth hormone, insulin, insulinotropin, insulin-like growth factors, parathyroid hormone, α2-interferon (IFNA2), β-interferon, γ-interferon, nerve growth factors, FSHβ, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-granulocyte (GCSF), CSF-macrophage, CSF-granulocyte/macrophage, immunoglobulins, catalytic antibodies, protein kinase C, glucocerebrosidase, superoxide dismutase, tissue plasminogen activator, urokinase, antithrombin III, DNAse, α-galactosidase, tyrosine hydroxylase, blood clotting factor V, blood clotting factor VII, blood clotting factor VIII, blood clotting factor IX, blood clotting factor X, blood clotting factor XIII, apolipoprotein E, apolipoprotein A-I, globins, low density lipoprotein receptor, IL-2 receptor, IL-2 antagonists, α-1-antitrypsin, immune response modifiers, β-glucoceramidase, α-iduronidase, α-L-iduronidase, glucosamine-N-sulfatase, α-N-acetylglucosaminidase, acetylcoenzymeA:α-glucosamine-N-acetyltransferase, N-acetylglucosamine-6-sulfatase, β-galactosidase, β-glucuronidase, N-acetylgalactosamine-6-sulfatase, and soluble CD4.

All patents and references cited herein are incorporated in their entirety by reference. Other embodiments are within the following claims.

What is claimed:

1. A complex for increasing homologous recombination of a target sequence in a cell, comprising: (a) a double stranded DNA sequence, (b) a homologous recombination-enhancing Rad52 protein or functional fragment thereof, and (c) a Ku-binding molecule which inhibits non-homologous end joining.

2. The complex of claim 1, wherein the Ku-binding molecule is selected from the group consisting of: an anti-Ku antibody, a Ku-binding oligomer, and a Ku-binding polypeptide.

3. The complex of claim 1, wherein the DNA sequence comprises a linear DNA sequence.

4. The complex of claim 1, wherein the DNA sequence is flanked by at least one targeting sequence.

5. The complex of claim 1, wherein the DNA sequence comprises an exogenous regulatory sequence.

6. The complex of claim 5, wherein the regulatory sequence is a promoter, an enhancer, an upstream activating sequence, a scaffold-attachment region or a transcription factor-binding site.

7. The complex of claim 5, wherein the regulatory sequence is a promoter and an enhancer.

8. The complex of claim 6, wherein the regulatory sequence is a promoter and an upstream activating sequence.

9. The complex of claim 1, wherein the Rad52 protein or functional fragment thereof is coated on the DNA sequence.

10. The complex of claim 1, wherein the Rad52 protein or fragment thereof is human Rad52.

11. The complex of claim 1, wherein the Ku-binding molecule is an anti-Ku antibody.

12. The complex of claim 11, wherein the anti-Ku antibody is an anti-Ku80 or anti-Ku70 antibody.

13. The complex of claim 11, wherein the anti-Ku antibody is covalently linked to the DNA sequence.

14. The complex of claim 11, wherein the anti-Ku antibody is covalently linked to the Rad52 protein or functional fragment thereof.

15. The complex of claim 11, wherein the complex comprises an anti-Ku70 antibody and an anti-Ku80 antibody.

16. The complex of claim 11, further comprising an agent which inhibits an Msh2 mismatch repair protein.

17. The complex of claim 4, wherein the DNA sequence comprises a regulatory sequence and the targeting sequence is derived from a sequence 5' of the protein coding region of the CFTR gene.

18. A method of increasing homologous recombination at a selected site in a target DNA of a cell, comprising: introducing into an isolated cell (a) a double stranded DNA sequence, (b) a Rad52 protein or functional fragment thereof, and (c) a Ku binding molecule, to thereby increase homologous recombination at a selected site in the chromosomal DNA.

19. The method of claim 18, wherein the DNA sequence comprises a linear DNA sequence.

20. The method of claim 18, wherein the DNA sequence is flanked by at least one targeting sequence.

21. The method of claim 18, wherein the DNA sequence comprises an exogenous regulatory sequence.

22. The method of claim 21, wherein the regulatory sequence selected from the group consisting of: a promoter, an enhancer, an upstream activating sequence, a scaffold-attachment region and a transcription factor-binding site.

23. The method of claim 21, wherein the regulatory sequence is a promoter and an enhancer.

24. The method of claim 21, wherein the regulatory sequence is a promoter and an upstream activating sequence.

25. The method of claim 18, wherein the Rad52 protein or functional fragment thereof is coated on the DNA sequence.

26. The method of claim 18, wherein the Rad52 protein or fragment thereof is human Rad52.

27. The method of claim 18, wherein the Ku-binding molecule is an anti-Ku antibody, a Ku-binding oligomer, or a Ku-binding polypeptide.

28. The method of claim 18, wherein the Ku-binding molecule is an anti-Ku antibody.

29. The method of claim 28, wherein the anti-Ku antibody is an anti-Ku70 antibody.

30. The method of claim 28, wherein the anti-Ku antibody is an anti-Ku80 antibody.

31. The method of claim 28, wherein the anti-Ku antibody is covalently linked to the DNA sequence.

32. The method of claim 28, wherein the anti-Ku antibody is covalently linked to the Rad52 protein or fragment thereof.

33. The method of claim 13, wherein the cell is a primary or secondary mammalian cell.

34. The method of claim 33, wherein the primary or secondary mammalian cell is a human cell.

35. The method of claim 18, wherein the DNA sequence, the Rad52 protein or functional fragment thereof and the Ku-binding molecule are introduced into the cell as a complex.

36. The method of claim 18, further comprising introducing an agent which inhibits an Msh2-mismatch-repair protein.

37. The method of claim 36, wherein the agent is an anti-Msh2 antibody.

38. The method of claim 37, wherein the anti-Msh2 antibody is covalently linked to the DNA sequence.

39. The method of claim 37, wherein the anti-Msh2 antibody is covalently linked to the Rad52 protein or fragment thereof.

40. The method of claim 16, wherein the target DNA comprises a mutation having less than 10 base pairs which differ from wild-type sequence.

41. The method of claim 40, wherein the mutation is a point mutation.

42. The method of claim 41, wherein the DNA sequence comprises a wild-type sequence which can correct the mutation.

43. The method of claim 42, wherein the target DNA is a cystic fibrosis transmembrane regulator (CFTR) gene.

44. The method of claim 43, wherein the mutation changes an amino acid encoded by codon 508 of the coding region of the CFTR gene.

45. A method of altering expression of a protein coding sequence of a gene in a cell, the method comprising:

introducing the complex of claim 1 into an isolated cell, wherein the DNA sequence comprises a regulatory sequence;

maintaining the cell under conditions which permit homologous recombination to produce a homologously recombinant cell; and maintaining the homologously recombinant cell under conditions which permit expression of the protein coding sequence of the gene under control of the regulatory sequence, thereby altering expression of the protein coding sequence of the gene.

46. The method of claim 20, wherein the DNA sequence comprises a regulatory sequence and the targeting sequence is derived from the region 5' of the CFTR coding region.

* * * * *

UNITED STATES PATENT AND TRADEMARK OFFICE
CERTIFICATE OF CORRECTION

PATENT NO. : 6,569,681 B1
DATED : May 27, 2003
INVENTOR(S) : Evguenii Ivanov

It is certified that error appears in the above-identified patent and that said Letters Patent is hereby corrected as shown below:

<u>Column 76,</u>
Line 58, change "5" to -- 6 --.

<u>Column 78,</u>
Line 4, change "13" to -- 18 --.
Line 22, change "16" to -- 18 --.

Signed and Sealed this

Fourth Day of April, 2006

JON W. DUDAS
*Director of the United States Patent and Trademark Office*